US009668868B2

(12) United States Patent
Shenoy et al.

(10) Patent No.: US 9,668,868 B2
(45) Date of Patent: *Jun. 6, 2017

(54) APPARATUS AND METHODS FOR TREATMENT OF PATELLOFEMORAL CONDITIONS

(71) Applicant: Cotera, Inc., Menlo Park, CA (US)

(72) Inventors: Vivek Shenoy, Redwood City, CA (US); Hanson S. Gifford, III, Redwood City, CA (US)

(73) Assignee: Cotera, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/644,792

(22) Filed: Mar. 11, 2015

(65) Prior Publication Data

US 2015/0196325 A1    Jul. 16, 2015

Related U.S. Application Data

(63) Continuation-in-part of application No. 13/002,829, filed as application No. PCT/US2010/046996 on (Continued)

(51) Int. Cl.
*A61F 2/38* (2006.01)
*A61B 17/56* (2006.01)
(Continued)

(52) U.S. Cl.
CPC ............ *A61F 2/38* (2013.01); *A61B 17/1659* (2013.01); *A61B 17/1675* (2013.01);
(Continued)

(58) Field of Classification Search
CPC ...... A61F 2002/4627; A61F 2002/4658; A61F 2002/30546; A61F 2002/30548;
(Continued)

(56) References Cited

U.S. PATENT DOCUMENTS 2,632,440 A    3/1953  Hauser
2,877,033 A    3/1959  Koetke
(Continued)

FOREIGN PATENT DOCUMENTS

CA    1205602    6/1986
CN    2788765    6/2006
(Continued)

OTHER PUBLICATIONS

Arnoczky et al., Biomechanical Analysis of Forces Acting About the Canine Hip, American Journal Veterinary Research, vol. 42, Issue: 9, Sep. 1981, pp. 1581-1585.
(Continued)

*Primary Examiner* — Ann Schillinger
(74) *Attorney, Agent, or Firm* — Downs Rachlin Martin PLLC

(57) ABSTRACT

Prostheses, methods and related instrumentation for treating disorders of the knee by displacing a connective tissue acting on the patella to alter the location, angle or magnitude of forces exerted by the tissue on the patella so as to achieve a therapeutic effect in patellofemoral compartment of the knee.

26 Claims, 20 Drawing Sheets

Related U.S. Application Data

Aug. 27, 2010, application No. 14/644,792, which is a continuation-in-part of application No. 13/843,128, filed on Mar. 15, 2013, now Pat. No. 9,278,004, which is a continuation-in-part of application No. 12/870,462, filed on Aug. 27, 2010, now Pat. No. 8,597,362.

(60) Provisional application No. 61/951,469, filed on Mar. 11, 2014, provisional application No. 61/951,470, filed on Mar. 11, 2014, provisional application No. 61/237,518, filed on Aug. 27, 2009, provisional application No. 61/288,692, filed on Dec. 21, 2009, provisional application No. 61/620,756, filed on Apr. 5, 2012, provisional application No. 61/695,406, filed on Aug. 31, 2012.

(51) Int. Cl.
  A61B 17/16 (2006.01)
  A61B 17/80 (2006.01)
  A61F 2/30 (2006.01)

(52) U.S. Cl.
  CPC .... *A61B 17/8061* (2013.01); *A61B 2017/564* (2013.01); *A61F 2/3877* (2013.01); *A61F 2002/30688* (2013.01)

(58) Field of Classification Search
  CPC .............. A61F 2002/30621; A61F 2/08; A61F 2/0805; A61F 2/0811; A61F 2/3872
  See application file for complete search history.

(56) References Cited

U.S. PATENT DOCUMENTS

| | | |
|---|---|---|
| 3,242,922 A | 3/1966 | Thomas |
| 3,648,294 A | 3/1972 | Shahrestani |
| 3,681,786 A | 8/1972 | Lynch |
| 3,779,654 A | 12/1973 | Horne |
| 3,872,519 A | 3/1975 | Giannestras et al. |
| 3,875,594 A | 4/1975 | Lynch |
| 3,879,767 A | 4/1975 | Stubstad |
| 3,886,599 A | 6/1975 | Schlien |
| 3,889,300 A | 6/1975 | Smith |
| 3,902,482 A | 9/1975 | Taylor |
| 3,964,106 A | 6/1976 | Hutter, Jr. et al. |
| 3,988,783 A | 11/1976 | Treace |
| 4,007,495 A | 2/1977 | Frazier |
| 4,041,550 A | 8/1977 | Frazier |
| 4,052,753 A | 10/1977 | Dedo |
| 4,054,955 A | 10/1977 | Seppo |
| 4,069,518 A | 1/1978 | Groth, Jr. et al. |
| 4,156,944 A | 6/1979 | Schreiber et al. |
| 4,158,894 A | 6/1979 | Worrell |
| 4,164,793 A | 8/1979 | Swanson |
| 4,187,841 A | 2/1980 | Knutson |
| 4,246,660 A | 1/1981 | Wevers |
| 4,285,070 A | 8/1981 | Averill |
| 4,308,863 A | 1/1982 | Fischer |
| 4,353,361 A | 10/1982 | Foster |
| 4,367,562 A | 1/1983 | Gauthier |
| 4,470,158 A | 9/1984 | Pappas et al. |
| 4,501,266 A | 2/1985 | McDaniel |
| 4,570,625 A | 2/1986 | Harris |
| 4,576,158 A | 3/1986 | Boland |
| 4,621,627 A | 11/1986 | DeBastiani et al. |
| 4,637,382 A | 1/1987 | Walker |
| 4,642,122 A | 2/1987 | Steffee |
| 4,696,293 A | 9/1987 | Ciullo |
| 4,759,765 A | 7/1988 | Van Kampen |
| 4,759,766 A | 7/1988 | Buettner-Janz et al. |
| 4,776,851 A | 10/1988 | Bruchman et al. |
| 4,778,472 A * | 10/1988 | Homsy .................. A61F 2/3099 623/17.17 |
| 4,846,842 A | 7/1989 | Connolly et al. |
| 4,863,471 A | 9/1989 | Mansat |
| 4,871,367 A | 10/1989 | Christensen et al. |
| 4,873,967 A | 10/1989 | Sutherland |
| 4,883,486 A | 11/1989 | Kapadia et al. |
| 4,904,261 A | 2/1990 | Dove et al. |
| 4,919,672 A | 4/1990 | Millar et al. |
| 4,923,471 A | 5/1990 | Morgan |
| 4,942,875 A | 7/1990 | Hlavacek et al. |
| 4,955,915 A | 9/1990 | Swanson |
| 4,959,065 A | 9/1990 | Arnett et al. |
| 4,988,349 A | 1/1991 | Pennig |
| 4,988,350 A | 1/1991 | Herzberg |
| 5,002,574 A | 3/1991 | May et al. |
| 5,011,497 A | 4/1991 | Persson et al. |
| 5,019,077 A | 5/1991 | DeBastiani et al. |
| 5,019,104 A | 5/1991 | Whiteside et al. |
| 5,026,372 A | 6/1991 | Sturtzkopf et al. |
| 5,035,700 A | 7/1991 | Kenna |
| 5,041,112 A | 8/1991 | Mingozzi et al. |
| 5,100,403 A | 3/1992 | Hotchkiss et al. |
| 5,103,811 A | 4/1992 | Crupi |
| 5,121,742 A | 6/1992 | Engen |
| 5,152,280 A | 10/1992 | Danieli |
| 5,152,790 A | 10/1992 | Rosenberg et al. |
| 5,197,966 A | 3/1993 | Sommerkamp |
| 5,197,986 A | 3/1993 | Mikhail |
| 5,231,977 A | 8/1993 | Graston |
| 5,258,032 A | 11/1993 | Bertin |
| 5,304,180 A | 4/1994 | Slocum |
| 5,314,481 A | 5/1994 | Bianco |
| 5,318,567 A | 6/1994 | Vichard |
| 5,326,364 A | 7/1994 | Clift, Jr. et al. |
| 5,352,190 A | 10/1994 | Fischer |
| 5,375,823 A | 12/1994 | Navas |
| 5,383,937 A | 1/1995 | Mikhail |
| 5,405,347 A | 4/1995 | Lee et al. |
| 5,415,661 A | 5/1995 | Holmes |
| 5,425,775 A | 6/1995 | Kovacevic et al. |
| 5,456,722 A | 10/1995 | McLeod et al. |
| 5,480,443 A | 1/1996 | Elias |
| 5,540,688 A | 7/1996 | Navas |
| 5,545,229 A | 8/1996 | Parsons et al. |
| 5,571,198 A | 11/1996 | Drucker et al. |
| 5,575,819 A | 11/1996 | Amis |
| 5,578,038 A | 11/1996 | Slocum |
| 5,580,353 A | 12/1996 | Mendes et al. |
| 5,601,553 A | 2/1997 | Trebling et al. |
| 5,624,440 A | 4/1997 | Huebner |
| 5,662,648 A | 9/1997 | Faccioli et al. |
| 5,662,650 A | 9/1997 | Bailey et al. |
| 5,676,667 A | 10/1997 | Hausman |
| 5,681,313 A | 10/1997 | Diez |
| 5,695,496 A | 12/1997 | Orsak et al. |
| 5,702,460 A | 12/1997 | Carls et al. |
| 5,702,465 A | 12/1997 | Burkinshaw |
| 5,702,467 A | 12/1997 | Gabriel et al. |
| 5,716,357 A | 2/1998 | Rogozinski |
| 5,733,287 A | 3/1998 | Tepic et al. |
| 5,749,872 A | 5/1998 | Kyle et al. |
| 5,766,251 A | 6/1998 | Koshino |
| 5,803,924 A | 9/1998 | Oni et al. |
| 5,824,106 A | 10/1998 | Fournol |
| 5,871,540 A | 2/1999 | Weissman et al. |
| 5,873,843 A | 2/1999 | Draper |
| 5,879,386 A | 3/1999 | Jore |
| 5,888,203 A | 3/1999 | Goldberg |
| 5,928,234 A | 7/1999 | Manspeizer |
| 5,976,125 A | 11/1999 | Graham |
| 5,976,136 A | 11/1999 | Bailey et al. |
| 5,989,292 A * | 11/1999 | van Loon .............. A61F 2/3099 623/17.17 |
| 6,036,691 A | 3/2000 | Richardson |
| 6,096,040 A | 8/2000 | Esser |
| 6,113,637 A | 9/2000 | Gill et al. |
| 6,132,468 A | 10/2000 | Mansmann |
| 6,139,550 A | 10/2000 | Michelson |
| 6,143,032 A | 11/2000 | Schafer et al. |
| 6,146,423 A | 11/2000 | Cohen et al. |

(56) References Cited

U.S. PATENT DOCUMENTS

| | | |
|---|---|---|
| 6,161,080 A | 12/2000 | Aouni-Ateshian et al. |
| 6,162,223 A | 12/2000 | Orsak et al. |
| 6,176,860 B1 | 1/2001 | Howard |
| 6,193,225 B1 | 2/2001 | Watanabe |
| 6,200,347 B1 | 3/2001 | Anderson et al. |
| D443,060 S | 5/2001 | Benirschke et al. |
| 6,245,110 B1 | 6/2001 | Grundei et al. |
| 6,264,696 B1 | 7/2001 | Reigner et al. |
| 6,277,124 B1 | 8/2001 | Haag |
| 6,280,474 B1 | 8/2001 | Cassidy et al. |
| 6,302,915 B1 | 10/2001 | Cooney, III et al. |
| 6,315,798 B1 | 11/2001 | Ashby et al. |
| 6,315,852 B1 | 11/2001 | Magrini et al. |
| 6,355,037 B1 | 3/2002 | Crosslin et al. |
| 6,364,881 B1 | 4/2002 | Apgar et al. |
| 6,368,326 B1 | 4/2002 | Dakin et al. |
| 6,371,985 B1 | 4/2002 | Goldberg |
| 6,409,729 B1 | 6/2002 | Martinelli et al. |
| 6,409,767 B1 | 6/2002 | Perice et al. |
| 6,468,314 B2 | 10/2002 | Schwartz et al. |
| 6,482,232 B1 | 11/2002 | Boucher et al. |
| 6,485,503 B2 | 11/2002 | Jacobs et al. |
| 6,494,914 B2 | 12/2002 | Brown et al. |
| 6,520,964 B2 | 2/2003 | Tallarida et al. |
| 6,527,733 B1 | 3/2003 | Ceriani et al. |
| 6,540,708 B1 | 4/2003 | Manspeizer |
| 6,572,653 B1 | 6/2003 | Simonson |
| 6,579,318 B2 | 6/2003 | Varga et al. |
| 6,589,248 B1 | 7/2003 | Hughes |
| 6,592,622 B1 | 7/2003 | Ferguson |
| 6,599,321 B2 | 7/2003 | Hyde, Jr. |
| 6,599,322 B1 | 7/2003 | Amrich et al. |
| 6,616,696 B1 | 9/2003 | Merchant |
| 6,620,332 B2 | 9/2003 | Amrich |
| 6,623,486 B1 | 9/2003 | Weaver et al. |
| 6,626,945 B2 | 9/2003 | Simon et al. |
| 6,632,247 B2 | 10/2003 | Boyer, II et al. |
| 6,652,529 B2 | 11/2003 | Swanson |
| 6,663,631 B2 | 12/2003 | Kuntz |
| 6,679,914 B1 | 1/2004 | Gabbay |
| 6,692,497 B1 | 2/2004 | Tormala et al. |
| 6,692,498 B1 | 2/2004 | Niiranen et al. |
| 6,702,821 B2 | 3/2004 | Bonutti |
| 6,709,460 B2 | 3/2004 | Merchant |
| 6,712,856 B1 | 3/2004 | Carignan et al. |
| 6,719,794 B2 | 4/2004 | Gerber |
| 6,752,831 B2 | 6/2004 | Sybert et al. |
| 6,770,078 B2 | 8/2004 | Bonutti |
| 6,800,094 B2 | 10/2004 | Burkinshaw |
| 6,814,757 B2 | 11/2004 | Kopylov et al. |
| 6,824,567 B2 | 11/2004 | Tornier et al. |
| 6,852,125 B2 | 2/2005 | Simon et al. |
| 6,852,330 B2 | 2/2005 | Bowman et al. |
| 6,854,330 B2 | 2/2005 | Potter |
| 6,855,150 B1 | 2/2005 | Linehan |
| 6,866,684 B2 | 3/2005 | Fell et al. |
| 6,884,242 B2 | 4/2005 | LeHuec et al. |
| 6,890,358 B2 | 5/2005 | Ball et al. |
| 6,893,463 B2 | 5/2005 | Fell et al. |
| 6,896,702 B2 | 5/2005 | Collazo |
| 6,905,513 B1 | 6/2005 | Metzger |
| 6,911,044 B2 | 6/2005 | Fell et al. |
| 6,916,341 B2 | 7/2005 | Rolston |
| 6,926,739 B1 | 8/2005 | O'Connor et al. |
| 6,966,910 B2 | 11/2005 | Ritland |
| 6,966,928 B2 | 11/2005 | Fell et al. |
| 6,972,020 B1 | 12/2005 | Grayson et al. |
| 6,974,480 B2 | 12/2005 | Messerli et al. |
| 6,994,730 B2 | 2/2006 | Posner |
| 6,997,940 B2 | 2/2006 | Bonutti |
| 7,004,971 B2 | 2/2006 | Serhan et al. |
| 7,008,452 B2 | 3/2006 | Hawkins |
| 7,011,687 B2 | 3/2006 | Deffenbaugh et al. |
| 7,018,418 B2 | 3/2006 | Amrich et al. |
| 7,025,790 B2 | 4/2006 | Parks et al. |
| 7,029,475 B2 | 4/2006 | Pajabi |
| 7,060,073 B2 | 6/2006 | Frey et al. |
| 7,105,025 B2 | 9/2006 | Castro et al. |
| 7,105,027 B2 | 9/2006 | Lipman et al. |
| 7,124,762 B2 | 10/2006 | Carter et al. |
| 7,128,744 B2 | 10/2006 | Weaver et al. |
| 7,141,073 B2 | 11/2006 | May et al. |
| 7,160,333 B2 | 1/2007 | Plouhar et al. |
| 7,163,563 B2 | 1/2007 | Schwartz et al. |
| 7,182,787 B2 | 2/2007 | Hassler et al. |
| 7,188,626 B2 | 3/2007 | Foley et al. |
| 7,201,728 B2 | 4/2007 | Sterling |
| 7,223,292 B2 | 5/2007 | Messerli et al. |
| 7,226,482 B2 | 6/2007 | Messerli et al. |
| 7,226,483 B2 | 6/2007 | Gerber et al. |
| 7,235,077 B1 | 6/2007 | Wang et al. |
| 7,235,102 B2 | 6/2007 | Ferree et al. |
| 7,238,203 B2 | 7/2007 | Bagga et al. |
| 7,241,298 B2 | 7/2007 | Nemec et al. |
| 7,247,157 B2 | 7/2007 | Prager et al. |
| 7,252,670 B2 | 8/2007 | Morrison et al. |
| 7,261,739 B2 | 8/2007 | Ralph et al. |
| 7,273,481 B2 | 9/2007 | Lombardo et al. |
| 7,276,070 B2 | 10/2007 | Muckter |
| 7,282,065 B2 | 10/2007 | Kirschman |
| 7,285,134 B2 | 10/2007 | Berry et al. |
| 7,288,094 B2 | 10/2007 | Lindemann et al. |
| 7,288,095 B2 | 10/2007 | Baynham et al. |
| 7,291,150 B2 | 11/2007 | Graf |
| 7,291,169 B2 | 11/2007 | Hodorek |
| 7,297,161 B2 | 11/2007 | Fell |
| 7,306,605 B2 | 12/2007 | Ross |
| 7,322,983 B2 | 1/2008 | Harris |
| 7,322,984 B2 | 1/2008 | Doubler et al. |
| 7,323,012 B1 | 1/2008 | Stone et al. |
| 7,341,589 B2 | 3/2008 | Weaver et al. |
| 7,341,590 B2 | 3/2008 | Ferree |
| 7,341,602 B2 | 3/2008 | Fell et al. |
| 7,361,196 B2 | 4/2008 | Fallin et al. |
| 7,476,225 B2 | 1/2009 | Cole |
| 7,479,160 B2 | 1/2009 | Branch et al. |
| 7,485,147 B2 | 2/2009 | Pappas et al. |
| 7,500,991 B2 | 3/2009 | Bartish, Jr. et al. |
| 7,534,270 B2 | 5/2009 | Ball |
| 7,544,210 B2 | 6/2009 | Schaefer et al. |
| 7,553,331 B2 | 6/2009 | Manspeizer |
| 7,572,291 B2 | 8/2009 | Gil et al. |
| 7,611,540 B2 | 11/2009 | Clifford et al. |
| 7,618,454 B2 | 11/2009 | Bentley et al. |
| 7,632,310 B2 | 12/2009 | Clifford et al. |
| 7,632,311 B2 | 12/2009 | Seedhom et al. |
| 7,637,953 B2 | 12/2009 | Branch et al. |
| 7,641,689 B2 | 1/2010 | Fell et al. |
| 7,655,029 B2 | 2/2010 | Niederberger et al. |
| 7,655,041 B2 | 2/2010 | Clifford et al. |
| 7,678,147 B2 | 3/2010 | Clifford et al. |
| 7,722,676 B2 | 5/2010 | Hanson et al. |
| 7,723,395 B2 | 5/2010 | Ringeisen et al. |
| 7,726,319 B1 | 6/2010 | Boyce |
| 7,744,638 B2 | 6/2010 | Orbay |
| 7,749,276 B2 | 7/2010 | Fitz |
| 7,758,651 B2 | 7/2010 | Chauhan et al. |
| 7,780,670 B2 | 8/2010 | Bonutti |
| 7,806,898 B2 | 10/2010 | Justin et al. |
| 7,819,918 B2 | 10/2010 | Malaviya et al. |
| 7,828,852 B2 | 11/2010 | Bonutti |
| 7,846,211 B2 | 12/2010 | Clifford et al. |
| 7,875,082 B2 | 1/2011 | Naidu |
| 7,879,105 B2 | 2/2011 | Schmieding et al. |
| 7,896,921 B2 | 3/2011 | Smith et al. |
| 7,896,923 B2 | 3/2011 | Blackwell et al. |
| 7,951,176 B2 | 5/2011 | Grady et al. |
| 7,959,675 B2 | 6/2011 | Gately |
| 7,967,863 B2 | 6/2011 | Frey et al. |
| 7,972,383 B2 | 7/2011 | Goldstein et al. |
| 7,993,402 B2 | 8/2011 | Sidler |
| 8,002,833 B2 | 8/2011 | Fabris Monterumici et al. |
| 8,002,837 B2 | 8/2011 | Stream et al. |
| 8,002,841 B2 | 8/2011 | Hasselman |

(56) References Cited

U.S. PATENT DOCUMENTS

| | | |
|---|---|---|
| 8,034,117 B2 | 10/2011 | Matsuzaki et al. |
| 8,043,375 B2 | 10/2011 | Strzepa et al. |
| 8,043,380 B1 | 10/2011 | Park et al. |
| 8,052,753 B2 | 11/2011 | Melvin |
| 8,052,755 B2 | 11/2011 | Naidu |
| 8,083,746 B2 | 12/2011 | Novak |
| 8,088,166 B2 | 1/2012 | Makower et al. |
| 8,088,168 B2 | 1/2012 | Hassler et al. |
| 8,092,530 B2 | 1/2012 | Strzepa et al. |
| 8,092,544 B2 | 1/2012 | Wright et al. |
| 8,100,967 B2 | 1/2012 | Makower et al. |
| 8,114,156 B2 | 2/2012 | Hatch |
| 8,123,805 B2 | 2/2012 | Makower et al. |
| 8,128,697 B2 | 3/2012 | Fell et al. |
| 8,128,704 B2 | 3/2012 | Brown et al. |
| 8,142,503 B2 | 3/2012 | Malone |
| 8,257,444 B2 | 9/2012 | Linares |
| 8,262,707 B2 | 9/2012 | Huebner et al. |
| 8,267,972 B1 | 9/2012 | Gehlert |
| 8,328,805 B2 | 12/2012 | Cole |
| 8,372,078 B2 | 2/2013 | Collazo |
| 8,382,807 B2 | 2/2013 | Austin et al. |
| 8,523,921 B2 | 9/2013 | Horan et al. |
| 8,523,948 B2 | 9/2013 | Slone et al. |
| 8,597,362 B2 | 12/2013 | Shenoy et al. |
| 8,845,724 B2 | 9/2014 | Shenoy et al. |
| 9,278,004 B2 * | 3/2016 | Shenoy ............... A61B 17/56 |
| 2001/0020143 A1 | 9/2001 | Stark et al. |
| 2001/0023371 A1 | 9/2001 | Bonutti |
| 2001/0037155 A1 | 11/2001 | Merchant |
| 2002/0013587 A1 | 1/2002 | Winquist et al. |
| 2002/0029045 A1 | 3/2002 | Bonutti |
| 2002/0029084 A1 | 3/2002 | Paul et al. |
| 2002/0052606 A1 | 5/2002 | Bonutti |
| 2002/0065560 A1 | 5/2002 | Varga et al. |
| 2002/0091447 A1 | 7/2002 | Shimp et al. |
| 2002/0095154 A1 | 7/2002 | Atkinson et al. |
| 2002/0107574 A1 | 8/2002 | Boehm et al. |
| 2002/0133230 A1 | 9/2002 | Repicci |
| 2002/0151978 A1 | 10/2002 | Zacouto et al. |
| 2002/0165550 A1 | 11/2002 | Frey et al. |
| 2003/0055500 A1 | 3/2003 | Fell et al. |
| 2003/0083751 A1 | 5/2003 | Tornier |
| 2003/0088315 A1 | 5/2003 | Supinski |
| 2003/0100950 A1 | 5/2003 | Moret |
| 2003/0109928 A1 | 6/2003 | Pasquet et al. |
| 2003/0120344 A1 | 6/2003 | Michelson |
| 2003/0120346 A1 | 6/2003 | Mercinek et al. |
| 2003/0125807 A1 | 7/2003 | Lambrecht et al. |
| 2003/0139813 A1 | 7/2003 | Messerli et al. |
| 2003/0204265 A1 | 10/2003 | Short et al. |
| 2003/0216809 A1 | 11/2003 | Ferguson |
| 2004/0054409 A1 | 3/2004 | Harris |
| 2004/0117020 A1 | 6/2004 | Frey et al. |
| 2004/0127990 A1 | 7/2004 | Bartish, Jr. et al. |
| 2004/0133278 A1 | 7/2004 | Marino et al. |
| 2004/0143336 A1 | 7/2004 | Burkinshaw |
| 2004/0143338 A1 | 7/2004 | Burkinshaw |
| 2004/0148026 A1 | 7/2004 | Bonutti |
| 2004/0167630 A1 | 8/2004 | Rolston |
| 2004/0172133 A1 | 9/2004 | Gerber et al. |
| 2004/0186585 A1 | 9/2004 | Feiwell |
| 2004/0215195 A1 | 10/2004 | Shipp et al. |
| 2004/0230303 A1 | 11/2004 | Gomes et al. |
| 2004/0230315 A1 | 11/2004 | Ek |
| 2004/0236428 A1 | 11/2004 | Burkinshaw et al. |
| 2004/0243240 A1 | 12/2004 | Beaurain et al. |
| 2004/0260302 A1 | 12/2004 | Manspeizer |
| 2004/0267179 A1 | 12/2004 | Leman |
| 2005/0004671 A1 | 1/2005 | Ross et al. |
| 2005/0027360 A1 | 2/2005 | Webb et al. |
| 2005/0033424 A1 | 2/2005 | Fell |
| 2005/0033426 A1 | 2/2005 | Ogilvie et al. |
| 2005/0043808 A1 | 2/2005 | Felt et al. |
| 2005/0049708 A1 | 3/2005 | Atkinson et al. |
| 2005/0049711 A1 | 3/2005 | Ball |
| 2005/0085815 A1 | 4/2005 | Harms et al. |
| 2005/0119664 A1 | 6/2005 | Carignan et al. |
| 2005/0119744 A1 | 6/2005 | Buskirk et al. |
| 2005/0137708 A1 | 6/2005 | Clark |
| 2005/0143822 A1 | 6/2005 | Paul |
| 2005/0143830 A1 | 6/2005 | Marcinek et al. |
| 2005/0154390 A1 | 7/2005 | Biedermann et al. |
| 2005/0192674 A1 | 9/2005 | Ferree |
| 2005/0222685 A1 | 10/2005 | Hayden et al. |
| 2005/0251080 A1 | 11/2005 | Hyde, Jr. |
| 2005/0261680 A1 | 11/2005 | Draper |
| 2005/0261767 A1 | 11/2005 | Anderson et al. |
| 2005/0267584 A1 | 12/2005 | Burdulis, Jr. et al. |
| 2005/0273114 A1 | 12/2005 | Novak |
| 2005/0288788 A1 | 12/2005 | Dougherty-Shah |
| 2006/0036321 A1 | 2/2006 | Henninger et al. |
| 2006/0064169 A1 | 3/2006 | Ferree |
| 2006/0074423 A1 | 4/2006 | Alleyne |
| 2006/0074492 A1 | 4/2006 | Frey |
| 2006/0085069 A1 | 4/2006 | Kim |
| 2006/0100715 A1 | 5/2006 | De Villiers |
| 2006/0106460 A1 | 5/2006 | Messerli et al. |
| 2006/0122620 A1 | 6/2006 | Kim |
| 2006/0129243 A1 | 6/2006 | Wong et al. |
| 2006/0142858 A1 | 6/2006 | Colleran et al. |
| 2006/0149274 A1 | 7/2006 | Justin et al. |
| 2006/0161260 A1 | 7/2006 | Thomas et al. |
| 2006/0178744 A1 | 8/2006 | de Villiers et al. |
| 2006/0235387 A1 | 10/2006 | Peterman |
| 2006/0276907 A1 | 12/2006 | Boyer, II et al. |
| 2007/0027547 A1 | 2/2007 | Rydell et al. |
| 2007/0043356 A1 | 2/2007 | Timm et al. |
| 2007/0106299 A1 | 5/2007 | Manspeizer |
| 2007/0129804 A1 | 6/2007 | Bentley et al. |
| 2007/0129809 A1 | 6/2007 | Meridew et al. |
| 2007/0161993 A1 | 7/2007 | Lowery et al. |
| 2007/0168033 A1 | 7/2007 | Kim et al. |
| 2007/0168036 A1 | 7/2007 | Ainsworth et al. |
| 2007/0173946 A1 | 7/2007 | Bonutti |
| 2007/0198088 A1 | 8/2007 | Biedermann et al. |
| 2007/0198091 A1 | 8/2007 | Boyer et al. |
| 2007/0203581 A1 | 8/2007 | Vanaclocha |
| 2007/0208343 A1 | 9/2007 | Magerl et al. |
| 2007/0225820 A1 | 9/2007 | Thomas et al. |
| 2007/0233141 A1 | 10/2007 | Park et al. |
| 2007/0244483 A9 | 10/2007 | Winslow et al. |
| 2007/0244488 A1 | 10/2007 | Metzger et al. |
| 2007/0265708 A1 | 11/2007 | Brown et al. |
| 2007/0288014 A1 | 12/2007 | Shadduck et al. |
| 2007/0293947 A1 | 12/2007 | Mansmann |
| 2007/0299528 A9 | 12/2007 | Lotke |
| 2008/0015591 A1 | 1/2008 | Castaneda et al. |
| 2008/0015592 A1 | 1/2008 | Long et al. |
| 2008/0015593 A1 | 1/2008 | Pfefferie et al. |
| 2008/0015603 A1 | 1/2008 | Collazo |
| 2008/0015604 A1 | 1/2008 | Collazo |
| 2008/0021566 A1 | 1/2008 | Peters et al. |
| 2008/0033552 A1 | 2/2008 | Lee et al. |
| 2008/0044449 A1 | 2/2008 | McKay |
| 2008/0071373 A1 | 3/2008 | Molz et al. |
| 2008/0071375 A1 | 3/2008 | Carver et al. |
| 2008/0091270 A1 | 4/2008 | Millet et al. |
| 2008/0097434 A1 | 4/2008 | Moumene et al. |
| 2008/0097441 A1 | 4/2008 | Hayes et al. |
| 2008/0097617 A1 | 4/2008 | Fellinger et al. |
| 2008/0132954 A1 | 6/2008 | Sekhon et al. |
| 2008/0140094 A1 | 6/2008 | Schwartz et al. |
| 2008/0140213 A1 | 6/2008 | Ammann et al. |
| 2008/0154311 A1 | 6/2008 | Staeubli |
| 2008/0154371 A1 | 6/2008 | Fell et al. |
| 2008/0154378 A1 | 6/2008 | Pelo |
| 2008/0161815 A1 | 7/2008 | Schoenefeld et al. |
| 2008/0161933 A1 | 7/2008 | Grotz et al. |
| 2008/0195099 A1 | 8/2008 | Minas |
| 2008/0200995 A1 | 8/2008 | Sidebotham |
| 2008/0234686 A1 | 9/2008 | Beaurain et al. |
| 2008/0262549 A1 | 10/2008 | Bennett et al. |
| 2008/0262618 A1 | 10/2008 | Hermsen et al. |

(56) References Cited

U.S. PATENT DOCUMENTS

| | | |
|---|---|---|
| 2008/0275509 A1 | 11/2008 | Clifford et al. |
| 2008/0275552 A1 | 11/2008 | Makower et al. |
| 2008/0275555 A1 | 11/2008 | Makower et al. |
| 2008/0275556 A1 | 11/2008 | Makower et al. |
| 2008/0275557 A1 | 11/2008 | Makower et al. |
| 2008/0275558 A1 | 11/2008 | Clifford et al. |
| 2008/0275559 A1 | 11/2008 | Makower et al. |
| 2008/0275560 A1 | 11/2008 | Clifford et al. |
| 2008/0275561 A1 | 11/2008 | Clifford et al. |
| 2008/0275562 A1 | 11/2008 | Clifford et al. |
| 2008/0275563 A1 | 11/2008 | Makower et al. |
| 2008/0275564 A1 | 11/2008 | Makower et al. |
| 2008/0275565 A1 | 11/2008 | Makower et al. |
| 2008/0275567 A1 | 11/2008 | Makower et al. |
| 2008/0275571 A1 | 11/2008 | Clifford et al. |
| 2008/0281422 A1 | 11/2008 | Schmieding |
| 2008/0281425 A1 | 11/2008 | Thalgott et al. |
| 2009/0012615 A1 | 1/2009 | Fell |
| 2009/0014016 A1 | 1/2009 | Clifford et al. |
| 2009/0018656 A1 | 1/2009 | Clifford et al. |
| 2009/0018665 A1 | 1/2009 | Clifford et al. |
| 2009/0036893 A1 | 2/2009 | Kartalian et al. |
| 2009/0048683 A1 | 2/2009 | Morris et al. |
| 2009/0088763 A1 | 4/2009 | Aram et al. |
| 2009/0088846 A1 | 4/2009 | Myung et al. |
| 2009/0112268 A1 | 4/2009 | Cole |
| 2009/0118830 A1 | 5/2009 | Fell |
| 2009/0164014 A1 | 6/2009 | Liljensten et al. |
| 2009/0182433 A1 | 7/2009 | Reiley et al. |
| 2009/0198341 A1 | 8/2009 | Choi et al. |
| 2009/0210063 A1 | 8/2009 | Barrett |
| 2009/0226068 A1 | 9/2009 | Fitz et al. |
| 2009/0248026 A1 | 10/2009 | Draper |
| 2009/0259311 A1 | 10/2009 | Shterling et al. |
| 2009/0259312 A1 | 10/2009 | Shterling et al. |
| 2009/0306783 A1 | 12/2009 | Blum |
| 2009/0312807 A1 | 12/2009 | Boudreault et al. |
| 2009/0318924 A1 | 12/2009 | Helenbolt et al. |
| 2009/0318976 A1 | 12/2009 | Gabriel et al. |
| 2010/0023126 A1 | 1/2010 | Grotz |
| 2010/0049322 A1 | 2/2010 | McKay |
| 2010/0049325 A1 | 2/2010 | Biedermann et al. |
| 2010/0057216 A1 | 3/2010 | Gannoe et al. |
| 2010/0076564 A1* | 3/2010 | Schilling .............. A61B 17/68 623/20.14 |
| 2010/0106247 A1 | 4/2010 | Makower et al. |
| 2010/0106248 A1 | 4/2010 | Makower et al. |
| 2010/0114322 A1 | 5/2010 | Clifford et al. |
| 2010/0121355 A1 | 5/2010 | Gittings et al. |
| 2010/0121457 A1 | 5/2010 | Clifford et al. |
| 2010/0125266 A1 | 5/2010 | Deem et al. |
| 2010/0131068 A1 | 5/2010 | Brown et al. |
| 2010/0131069 A1 | 5/2010 | Halbrecht |
| 2010/0137996 A1 | 6/2010 | Clifford et al. |
| 2010/0145449 A1 | 6/2010 | Makower et al. |
| 2010/0161057 A1 | 6/2010 | Berry et al. |
| 2010/0168857 A1 | 7/2010 | Hatch |
| 2010/0198354 A1 | 8/2010 | Halbrecht |
| 2010/0204798 A1 | 8/2010 | Gerbec et al. |
| 2010/0262246 A1 | 10/2010 | Attia |
| 2010/0292731 A1 | 11/2010 | Gittings et al. |
| 2010/0292733 A1 | 11/2010 | Hendricksen et al. |
| 2010/0305698 A1 | 12/2010 | Metzger et al. |
| 2010/0305708 A1 | 12/2010 | Lang et al. |
| 2011/0004305 A1 | 1/2011 | Jansson et al. |
| 2011/0054627 A1 | 3/2011 | Bear |
| 2011/0060422 A1 | 3/2011 | Makower et al. |
| 2011/0093073 A1 | 4/2011 | Gatt et al. |
| 2011/0093079 A1 | 4/2011 | Slone et al. |
| 2011/0093080 A1 | 4/2011 | Slone et al. |
| 2011/0121457 A1 | 5/2011 | Clevenger et al. |
| 2011/0137415 A1 | 6/2011 | Clifford et al. |
| 2011/0172768 A1 | 7/2011 | Cragg et al. |
| 2011/0202138 A1* | 8/2011 | Shenoy ............... A61B 17/56 623/20.14 |
| 2011/0213466 A1 | 9/2011 | Shenoy et al. |
| 2011/0224734 A1 | 9/2011 | Schelling |
| 2011/0230919 A1 | 9/2011 | Alleyne |
| 2011/0238180 A1 | 9/2011 | Fritz et al. |
| 2011/0245928 A1 | 10/2011 | Landry et al. |
| 2011/0264216 A1 | 10/2011 | Makower et al. |
| 2011/0270393 A1 | 11/2011 | Marvel |
| 2011/0288643 A1 | 11/2011 | Linder-Ganz et al. |
| 2012/0022649 A1 | 1/2012 | Robinson et al. |
| 2012/0022655 A1 | 1/2012 | Clifford |
| 2012/0046754 A1 | 2/2012 | Clifford et al. |
| 2012/0053644 A1 | 3/2012 | Landry et al. |
| 2012/0065640 A1 | 3/2012 | Metzger et al. |
| 2012/0116522 A1 | 5/2012 | Makower et al. |
| 2012/0136449 A1 | 5/2012 | Makower et al. |
| 2012/0179273 A1 | 7/2012 | Clifford et al. |
| 2012/0197410 A1* | 8/2012 | Horan ............... A61B 17/68 623/20.32 |
| 2012/0221106 A1 | 8/2012 | Makower et al. |
| 2012/0271366 A1 | 10/2012 | Katrana et al. |
| 2012/0290088 A1 | 11/2012 | Amirouche et al. |
| 2013/0013066 A1 | 1/2013 | Landry et al. |
| 2013/0013067 A1 | 1/2013 | Landry et al. |
| 2013/0041416 A1 | 2/2013 | Regala et al. |
| 2013/0096629 A1 | 4/2013 | Rollinghoff et al. |
| 2013/0150977 A1 | 6/2013 | Gabriel et al. |
| 2013/0166036 A1 | 6/2013 | De Cortanze et al. |
| 2013/0190886 A1 | 7/2013 | Tepic et al. |
| 2013/0204378 A1 | 8/2013 | Slone et al. |
| 2013/0211521 A1* | 8/2013 | Shenoy ............... A61B 17/56 623/13.12 |
| 2013/0289728 A1 | 10/2013 | Makower et al. |
| 2013/0304208 A1 | 11/2013 | Clifford et al. |
| 2013/0325123 A1 | 12/2013 | Clifford et al. |
| 2013/0338783 A1 | 12/2013 | Slone et al. |
| 2014/0052266 A1 | 2/2014 | Slone et al. |
| 2014/0156004 A1 | 6/2014 | Shenoy et al. |
| 2014/0156005 A1 | 6/2014 | Shenoy et al. |
| 2014/0257292 A1 | 9/2014 | Embleton et al. |

FOREIGN PATENT DOCUMENTS

| | | |
|---|---|---|
| DE | 19855254 A1 | 6/2000 |
| EP | 0383419 A1 | 8/1990 |
| EP | 0953317 B1 | 4/2004 |
| EP | 1410769 A2 | 4/2004 |
| EP | 1770302 A1 | 4/2007 |
| EP | 1429675 B1 | 10/2007 |
| EP | 1682020 B1 | 10/2007 |
| EP | 1847228 A1 | 10/2007 |
| EP | 1847229 A2 | 10/2007 |
| EP | 1005290 B1 | 2/2008 |
| EP | 1468655 B1 | 5/2008 |
| EP | 2452641 A1 | 5/2012 |
| FR | 2926456 A1 | 7/2009 |
| GB | 1507953 | 4/1978 |
| GB | 2223406 | 4/1990 |
| GB | 2250919 | 10/1993 |
| JP | 59131348 | 7/1984 |
| JP | 7100159 | 4/1995 |
| JP | 2532346 B2 | 11/1996 |
| JP | 2000503865 | 4/2000 |
| JP | 2001145647 | 5/2001 |
| JP | 2003102744 | 4/2003 |
| JP | 2006280951 | 10/2006 |
| JP | 2007167318 | 7/2007 |
| JP | 2007167319 | 7/2007 |
| JP | 2007170969 | 7/2007 |
| NZ | 533300 | 2/2005 |
| RU | 1769868 A1 | 10/1992 |
| RU | 2085148 | 7/1997 |
| RU | 2217105 C2 | 11/2003 |
| RU | 2241400 C2 | 12/2004 |
| SU | 578063 A1 | 10/1977 |
| SU | 578957 A1 | 11/1977 |
| SU | 624613 A1 | 9/1978 |
| SU | 640740 A1 | 1/1979 |
| SU | 704605 A1 | 12/1979 |
| SU | 719612 A1 | 3/1980 |

(56) References Cited

FOREIGN PATENT DOCUMENTS

| | | |
|---|---|---|
| SU | 741872 A1 | 6/1980 |
| SU | 1186204 | 10/1985 |
| SU | 1251889 | 8/1986 |
| SU | 1316666 A1 | 6/1987 |
| SU | 1588404 | 8/1990 |
| SU | 1699441 A1 | 12/1991 |
| WO | 91/07137 | 5/1991 |
| WO | 94/06364 A1 | 3/1994 |
| WO | 96/19944 A1 | 7/1996 |
| WO | 2004019831 A2 | 3/2004 |
| WO | 2004024037 A2 | 3/2004 |
| WO | 2006045091 A2 | 4/2006 |
| WO | 2006049993 | 5/2006 |
| WO | 2006110578 A3 | 10/2006 |
| WO | 2007056645 A2 | 5/2007 |
| WO | 2007090009 A1 | 8/2007 |
| WO | 2007090015 A1 | 8/2007 |
| WO | 2007090017 A1 | 8/2007 |
| WO | 2007106962 A1 | 9/2007 |
| WO | 2007109132 A2 | 9/2007 |
| WO | 2007109140 A2 | 9/2007 |
| WO | 2007109417 A2 | 9/2007 |
| WO | 2007109436 A2 | 9/2007 |
| WO | 2007114769 A1 | 10/2007 |
| WO | 2007117571 A2 | 10/2007 |
| WO | 2008006098 A2 | 1/2008 |
| WO | 2009018365 A1 | 2/2009 |
| WO | 2011025959 A1 | 3/2011 |
| WO | 2012062908 A1 | 5/2012 |

OTHER PUBLICATIONS

Becker et al., Surgical Treatment of Isolated Patellofemoral Osteoarthritis, Clinical Orthopaedics and Related Research vol. 466, No. 2, Feb. 2008, pp. 443-449.
Cerejo et al., The Influence of Alignment on Risk of Knee Osteoarthritis Progression According to Baseline Stage of Disease, Arthritis & Rheumatism, vol. 46, No. 10, Oct. 2002, pp. 2632-2636.
Clifford et al., The KineSpring load absorber implant: Rationale, Design and Biomechanical Characterization, Journal of Medical Engineering & Technology, vol. 35, No. 1, Jan. 2011, pp. 65-71.
Delp et al., An Interactive Graphics-Based Model of the Lower Extremity to Study Orthopaedic Surgical Procedures, IEEE Transactions on Biomedical Engineering, vol. 37, No. 8, Aug. 1990, pp. 757-767.
Delp et al., Biomechanical Analysis of the Chiari Pelvic Osteotomy Preserving Hip Abductor Strength, Reprinted from Clinical Orthopaedics, vol. 25, May 1990, pp. 189-198.
Free et al, Trochanteric Transfer in Total Hip Replacement: Effects on the Moment Arms and Force-Generating Capacities of the Hip Abductors, Journal of Orthopaedic Research, vol. 14, No. 2, 1996, pp. 245-250.
Jack Farr, M.D., Tibial Tubercle Osteotomy, Techniques in Knee Surgery, vol. 2, Issue 1, 2003, pp. 28-42.
Goetz et al., Hip Joint Contact Force in the Emu (*Dromaius novaehollandiae*) during Normal Level Walking, Journal of Biomechanics, 41(4), 2008, pp. 770-778.
Jacobsen et al., Hip dysplasia: a significant risk factor for the development of hip osteoarthritis. A cross-sectional survey, Rheumatology vol. 44 No. 2, 2005, pp. 211-218.
Jingushi et al., Transtrochanteric Valgus Osteotomy for the Treatment of Osteoarthritis of the Hip Secondary to Acetabular Dysplasia, The Journal of Bone & Joint Surgery [Br], vol. 84-B, No. 4, May 2002, pp. 535-539.
Kirkley et al., The Effect of Bracing on Varus Gonarthrosis, The Journal of Bone and Joint Surgery, vol. 81-A, No. 4, Apr. 1999, pp. 539-548.
Lafeber et al., Unloading Joints to Treat Osteoarthritis, including Joint Distraction, Current Opinion in Rheumatology 2006, 18, pp. 519-525.

Lloyd et al., An EMG-driven Musculoskeletal Model to Estimate Muscle Forces and Knee Joint Moments in Vivo, Journal of Biomechanics 36, 2003, pp. 765-776.
Lloyd et al., Strategies of Muscular Support of Varus Andvalgus Isometric Loads at the Human Knee, Journal of Biomechanics 34, 2001, pp. 1257-1267.
Maquet, P, Biomechanics of Hip Dysplasia, Acta Ortopaedica Belgica, vol. 65-3, 1999, pp. 302-314.
McWilliams et al., Mild Acetabular Dysplasia and Risk of Osteoarthritis of the hip: a case-control study, Annals of the Rheumatic Diseases, 2010; 69, pp. 1774-1778.
Merritt et al., Influence of Muscle-Tendon Wrapping on Calculations of Joint Reaction Forces in the Equine Distal Forelimb, Journal of Biomedicine and Biotechnology, vol. 2008, Article ID 165730, 9 pages.
Pedersen et al., A Model to Predict Canine Pelvic Limb Musuloskeletal Geometry, Acta Anat 1991; 140, pp. 139-145.
Pollo et al., Knee Bracing for Unicompartmental Osteoarthritis, Journal of the American Academy of Orthopaedic Surgeons, vol. 14, No. 1, Jan. 2006, pp. 5-11.
Pollo et al., Reduction of Medial Compartment Loads with Valgus Bracing of the Osteoarthritic Knee, The American Journal of Sports Medicine, vol. 30, No. 3, 2002, pp. 414-421.
Saleh et al., Operative Treatment of Patellofemoral Arthritis, The Journal of Bone & Joint Surgery, vol. 87-A, No. 3, Mar. 2005, pp. 659-671.
Sharma et al., The Role of Knee Alignment in Disease Progression and Functional Decline in Knee Osteoarthritis, JAMA, vol. 286, No. 2, Jul. 11, 2001, pp. 188-195.
Sims et al., Investigation of Hip Abductor Activation in Subjects with Clinical Unilateral Hip Osteoarthritis, Annals of the Rheumatic Diseases, 2002; 61: pp. 687-692.
Thorp et al., The biomechanical effects of focused muscle training on medial knee loads in OA of the knee: a pilot, proof of concept study, Journal of Musculoskeletal and Neuronal Interactions, 10(2): 2010, pp. 166-173.
Wenger et al., Early Surgical Correction of Residual Hip Dysplasia: The San Diego Children's Hospital Approach, Acta Orthopaedica Belgica, vol. 65, 1999, pp. 277-287.
Winby et al., Muscle and External Load Contribution to Knee Joint Contact Loads during Normal Gait, Journal of Biomechanics 42, 2009, pp. 2294-2300.
Response to Final Office Action dated Apr. 1, 2013, in connection with related U.S. Appl. No. 13/002,829 International filing date Aug. 27, 2010.
Amendment and Response to Final Office Action dated May 20, 2013, in connection with related U.S. Appl. No. 12/870,462, filed Aug. 27, 2010.
Advisory Action dated Apr. 23, 2013 in connection with related U.S. Appl. No. 13/002,829, filed Jan. 6, 2011.
Advisory Action dated Jun. 20, 2013 in connection with related U.S. Appl. No. 13/002,829, filed Jan. 6, 2011.
Tew, M et al.; Anteriorization of the quadriceps tendon. A biomechanical study on a new technique for unloading the patellofemoral joint. University of Tennessee College of Medicine; Poster No. 0848 • ORS 2012 Annual Meeting.
Miller, R.K., Goodfellow, J.W., Murray, D.W. and O'Connor, J.J., In vitro measurement of patellofemoral force after three types of knee replacement; The Journal of Bone & Joint Surgery (Br), vol. 80-B, No. 5, Sep. 1998; pp. 900-906.
Ganesh, V.K., et al., Biomechanics of bone-fracture fixation by stiffness-graded plates in comparison with stainless-steel plates, Biomedical Engineering Online, 2005, 4:46, 15 pgs.
Benli, Semih et al., Evaluation of bone plate with low-stiffness material in terms of stress distribution, Journal of Biomechanics, 41 (2008) 3229-3235.
Haase, Kristina et al., A Discussion on Plating Factors that Affect Stress Shielding Using Finite Element Analysis, Journal of Biomechanical Science and Engineering, vol. 5, No. 2, 2010, pp. 129.
Anatomic Locked Plating System Brochure, BIOMET® Orthopedics, Form BMET0002.0, REV 053112, pp. 1-16, Copyright 2012.

(56) References Cited

OTHER PUBLICATIONS

SPS Periarticular Plates Brochure, STRYKER® Trauma AG, Literature No. 982274, Lot B46404, pp. 1-8; Copyright 2004.
Zimmer® Periarticular Distal Femoral Locking Plate Surgical Technique, the Science of the Landscape, Zimmer, 97-2347-044-00 Rev. 1 7.5 ML; pp. 1-20; Copyright 2005.
Hessmann et al., Compression Plate With or Without Lag Screw; AO Surgery Reference—Online reference in clinical life; Distal Tibia—Reduction & Fixation—Compression Plate; https://www2.aofoundation.org/wps/portal; pp. 1-9; Dec. 3, 2008.
LCP Locking Compression Plate—Ordering Information; SYNTHES®, 036.000.017, SE_042064 AD, 31080015; pp. 1-68; Copyright 2008.
Plates for 4.5 mm and 6.5 mm Screws; Raj Surgical Works; http://www.orthoindustries.com/plates-for-4-5-mm-and-6-5-mm-screws.html; pp. 1-8; printed Nov. 19, 2012.
Final (Rejection) Office Action dated Mar. 18, 2013, in connection with related U.S. Appl. No. 12/870,462, filed Aug. 27, 2010.
Final Office Action dated Jan. 31, 2013, in connection with related U.S. Appl. No. 13/002,829, filed Jan. 6, 2011.
PCT International Search Report and Written Opinion dated Jan. 9, 2014, for related application PCT/US2013/058877 filed Sep. 10, 2013 entitled "Method and Apparatus for Treating Canine Cruciate Ligament Disease," Vivek Shenoy.
Bruce et al., "Patellar Contact Pressure Changes with Anteromedialization of Tibial Tubercle, Lateral Release, and New Technique for Elevating Quadriceps Tendon: A Biomechanical Study," Journal of Surgical Orthopaedic Advances 22(4), pp. 270-276, 2013.
Response to Non-Final Office Action dated May 26, 2015, in connection with related U.S. Appl. No. 13/002,829, filed Jan. 6, 2011.
Response to Non-Final Office Action dated Apr. 20, 0215, in connection with related U.S. Appl. No. 13/843,128, filed Mar. 15, 2013.
Final Office Action dated Jun. 10, 2015, in connection with related U.S. Appl. No. 13/843,128, filed Mar. 15, 2013.
Partial International Search dated May 11, 2015, in connection with related PCT/US2015/019938, filed Mar. 11, 2015.
Synthes, Inc., LCP Proximal Tibial Plate 3.5; Technique Guide; pp. 1-20; Jun. 2011.
Synthes TomoFix Osteotomy System Technique Guide. A comprehensive plating system for stable fixation of osteotomies around the knee. 38 pages.
LOQTEQ Anatomical Plating System Design Rationale. Locking Compression Technology by aap. aap Implantate AG. 11 pages.
Response to Election/Restriction dated Jul. 1, 2014 in connection with related U.S. Appl. No. 14/175,813, filed Feb. 7, 2014.
Office Action dated Jul. 9, 2012, in connection with related European Application No. 10812664, entitled Method and Apparatus for Force Redistributon in Articular Joints, filed Aug. 27, 2010, Cotera, Inc.
Maquet, P., Biomechanical Treatment of Patellofemoral Osteoarthritis. Advancement of the Patellar Tendon; Review of Rheumatism and Osteoarticular Diseases, National Library of Medicine, Dec. 1963, vol. 30, Issue 12, pp. 780-785.
Maquet, Paul G.J., Biomechanics of the Knee With Application to the Pathogenesis and the Surgical Treatment of Osteoarthritis; Springer-Verlag Berlin Heidelberg New York, 1976, pp. 134-204.
Sridhar et al., Obesity and symptomatic osteoarthritis of the knee, The Journal of Bone & Joint Surgery, Instructional Review, vol. 94-B, No. 4, Apr. 2012, pp. 433-441.
Lasmar, et al., Importance of the Different Posterolateral Knee Static Stabilizers: Biomechanical Study; Clinics 2010; 65(4) pp. 433-440.
Hunter, David et al., Alignment and Osteoarthritis of the Knee, Journal of Bone and Joint Surgery, 2009: 91 Suppl. 1:85-9, pp. 85-89.
Halbrecht, Jeffrey L., Arthroscopic Patella Realignment: An All-Inside Technique, Arthroscopy: The Journal of Arthroscopic and Related Surgery, vol. 17, No. 9 Nov.-Dec. 2001; pp. 940-945.
Arnold, Allison S., et al., Do the hamstrings operate at increased muscle-tendon lengths and velocities after surgical lengthening? Journal of Biomechanics, Mar. 2005; pp. 1-9.
Unnanuntana, Aasis et al., Management of chronic lateral instability due to lateral collateral ligament deficiency after total knee arthroplasty: a case report; Journal of Medical Case Reports, 2010, 4:144; pp. 1-5.
Maquet, P., Biomechanical Aspects of the Relationship between Femur and Patella, Z. Orthop. 112 (1974); pp. 620-623.
Kwak, et al., Hamstrings and Iliotibial Band Forces Affect Knee Kinematics and Contact Pattern, Journal of Orthopaedic Research, 18: 101-108; The Journal of Bone and Joint Surgery, Inc. 1999.
Maquet P., Reduction of the articular pressure of the hip by surgical lateralization of the greater trochanter, PMID: 1015273, Clin Orthop Relat Res. Mar.-Apr. 1977; (123): 138 (Abstract only).
Maquet P., Importance of the position of the greater trochanter, PMID: 2382566, Acta Orthop Belg. 1990; 56 (1 Pt. B): 307 (Abstract only).
Maquet, Paul, "Advancement of the Tibial Tubersosity," Clinical Orthopaedics and Related Research, No. 15, 1976, pp. 225-230.
Townsend et al., "The Biomechanics of the Human Patella and its Implications for Chodromalacia," Journal of Biomechanics, 1977, vol. 10, pp. 403-407.
Supplementary European Search Report dated May 23, 2012 for related application EP10812664 filed Aug. 27, 2010, entitled "Method and Apparatus for Force Redistribution in Articular," Cotera, Inc.
Non-Final Office Action dated Apr. 11, 2014, in connection with related U.S. Appl. No. 14/175,829, filed Feb. 2, 2014, Vivek Shenoy.
Final Office Action dated Feb. 26, 2015, in connection with related U.S. Appl. No. 13/002,829, filed Jan. 6, 2011.
Notice of Allowance dated Feb. 3, 2015, in connection with related U.S. Appl. No. 14/175,813, filed Feb. 7, 2014.
PCT International Search Report and Written Opinion dated Oct. 20, 2010, for related application PCT/US2010/046996 filed Aug. 27, 2010 entitled "Method and Apparatus for Force Redistribution in Articular Joints"; Vivek Shenoy, Mark Deem and Hanson Gifford.
Office Action dated May 17, 2012, in connection with related U.S. Appl. No. 13/002,829, filed Jan. 6, 2011, Shenoy.
Office Action dated Jul. 24, 2012, in connection with related U.S. Appl. No. 12/870,462, filed Aug. 27, 2010, Shenoy.
Final (Rejection) Office Action dated Jan. 31, 2013, in connection with related U.S. Appl. No. 13/002,829, filed Jan. 6, 2011.
Lapinskaya, Valentina Spiridonovna, "Treatment of Diseases and Injuries of Hip Joint Using a Method of Distraction", Kuibyshev Medical Institute, 1990.
Larionov D. Yu, et al., "Medical Devices," Scientific and Technical Bimonthly Journal, May-Jun. 2008.
Lapinskaya, V.S., et al., "An Endoapparatus for Restoration of the Hip Joint," Writers Collective, 2008, UDK 615.472.03:616.728.2-089.28; pp. 8-12.
Tomita, Naohide, "Development of Treatment Devices for Cartilage Regeneration", BME vol. 16, No. 2.
Lentsner, A.A., et al., "Device for Functional Relief of Hip Joint in Cotyloid Cavity Fracture Cases", Ortop Travmatol Protez. Apr. 1990 (4) 44-6.
Aldegheri, Roberto, M.C., et al.; "Articulated Distraction of the Hip Conservative Surgery for Arthritis in Young Patients," Clinical Orthopaedics and Related Research, No. 301, pp. 94-101.
Andriacchi, Thomas P., Ph.D. et al.; "Methods for Evaluating the Progression of Osteoarthritis"; Journal of Rehabilitation Research and Development, vol. 37, No. 2., Mar./Apr. 2000, pp. 163-170.
Arendt, Elizabeth, M.D.; "Anatomy and Malalignment of the Patellofemoral Joint—Its Relation to Patellofemoral Arthrosis"; Clinical Orthopaedics and Related Research; 2005, No. 436, pp. 71-75.
Benzel, Edward; "Qualitative Attributes of Spinal Implants"; in: Biomechanics of Spine Stabilization, 1995, pp. 137-150.

(56) References Cited

OTHER PUBLICATIONS

Buckwalter, Joseph A.; "Joint Distraction for Osteoarthritis"; The Lancet, Department of Orthopaedic Surgery, University of Iowa Hospitals and Clinics, vol. 347, Feb. 3, 1996, pp. 279-280.

Coathup, M.J. et al.; "Osseo-mechanical induction of extra-cortical plates with reference to their surface properties and gemoetric designs", Elsevier, Biomaterials 20 (1999) pp. 793-800.

Deie, Masataka, M.D. et al.; "A New Articulated Distraction Arthroplasty Device for Treatment of the Osteoarthritic Knee Joint: A Preliminary Report"; Arthroscopy: The Journal of Arthroscopic and Related Surgery; vol. 23, No. 8 Aug. 2007: pp. 833-838.

Dienst, M. et al.; "Dynamic External Fixation for Distal Radius Fractures"; Clinical Orthopaedics and Related Research, 1997, vol. 338, pp. 160-171.

Gunther, Klaus-Peter, M.D.; "Surgical Approaches for Osteoarthritis"; Best Practice & Research Clinical Rheumatology, vol. 15, No. 4, 2001, pp. 627-643.

Hall, J. et al.; "Use of a Hinged External Fixator for Elbow instability after Severe Distal Humeral Fracture"; Journal of Orthopaedic Trauma, 2000, vol. 14, No. 6, pp. 442-448.

Klein, D. et al.; "Percutaneous Treatment of Carpal, Metacarpal, and Phalangeal Injuries"; Clinical Orthopaedics and Related Research, 2000, vol. 375, pp. 116-125.

Krakauer J. et al.; "Hinged Device for Fractures involving the Proximal Interphalangeal Joint"; Clinical Orthopaedics and Related Research, 1996, vol. 327, pp. 29-37.

Leon, Heriberto Ojeda, M.D. et al.; "Minimally Invasive Selective Osteotomy of the Knee: A New Surgical Technique"; Arthroscopy: The Journal of Arthroscopic and Related Surgery, vol. 17, No. 5 May-Jun. 2001: pp. 510-516.

Madey, S. et al.; "Hinged External Fixation of the elbow: optimal axis alignment to minimize motion resistance"; Journal of Orthopaedic Trauma, 2000, vol. 14, No. 1, pp. 41-47.

Neel, Michael D., M.D. et al.; "Early Multicenter Experience With a Noninvasive Expandable Prosthesis"; Clinical Orthopaedics and Related Research, 2003, No. 415, pp. 72-81.

Neel, Michael D., M.D.; "Repiphysis—Limb Salvage System for the Skeletally Immature"; Wright Medical Technology, Reiphiphysis Limb Salvage System, 2004, pp. 1-8.

Nockels, Russ P.; "Dynamic Stabilization in the Surgical Management of Painful Lumbar Spinal Disorders"; Spine, 2005, vol. 30, No. 16S, pp. S68-S72.

Orthofix; "Xcaliber Articulated Ankle"; advertising brochure, May 2004.

Orthofix; "Gentle Limb Deformity Correction"; website pages, http://www.eight-plate.com/, 2008.

Perry, Clayton R. et al.; "Patellar Fixation Protected with a Load-Sharing Cable: A Mechanical and Clinical Study"; Journal of Orthopaedic Trauma, 1988, vol. 2, No. 3, pp. 234-240.

Pilliar et al., "Bone Ingrowth and Stress Shielding with a Porous Surface Coated Fracture Fixation Plate," Journal of Biomedical Materials Research, vol. 13, (1979), pp. 799-810.

Repicci, John A., M.D. et al. "Minimally Invasive Unicondylar Knee Arthroplasty for the Treatment of Unicompartmental Osteoarthritis: an outpatient arthritic bypass procedure"; Orthopedic Clinics of North America, 35 (2004), pp. 201-216.

Sharma, Leena et al. "The Mechanism of the Effect of Obesity in Knee Osteoarthritis—The Mediating Role of Malalignment"; Arthritis & Rheumatism, vol. 43, No. 3, Mar. 2000, pp. 568-575.

Sommerkamp, G. et al.; "Dynamic External Fixation of Unstable Fractures of the Distal Part of the Radius"; The Journal of Bone and Joint Surgery; Aug. 1994, vol. 76-A, No. 8, pp. 1149-1161.

Tencer, Allan F. et al. "Fixation of the Patella (Chap. 9.3)"; in: Biomechanics in Orthopedic Trauma Bone Fracture and Fixation, 1994.

Thakur, A.J.; "Tension Band Wiring"; in; The Elements of Fracture Fixation, 1997, pp. 126-146.

Uchikura, C. et al.; "Comparative Study of Nonbridging and Bridging External Fixators from Unstable Distal Radius fractures"; Journal of Orthopaedic Science, 2004, vol. 9, No. 6, pp. 560-565.

Van Der Esch, M. et al.; "Structural Joint Changes, Malalignment, and Laxity in Osteoarthritis of the knee"; Scand J Rheumatol 2005; 34: pp. 298-301.

Weisstein, Jason S., M.D. et al.; "Oncologic Approaches to Pediatric Limb Preservation"; Journal of the American Academy of Orthopaedic Surgeons; vol. 13, No. 8, Dec. 2005, pp. 544-554.

Wilke, Hans-Joachim et al.; "Biomechanical Evaluation of a New Total Posterior-Element Replacement System"; Spine, 2006, vol. 31, No. 24, pp. 2790-2796.

Wilkins, Ross M., M.D. et al. "The Phenix Expandable Prosthesis"; Clinical Orthopaedics and Related Research, No. 382, pp. 51-58.

Yamamoto, Ei et al.; "Effects of Stress Shielding on the Transverse Mechanical Properties of Rabbit Patellar Tendons"; Journal of Biomechanical Engineering, 2000, vol. 122, pp. 608-614.

Nagai, et al., "B109 Mobility Evaluation of Hip-Joint Nonweight-Bearing Device," The Japan Society of Mechanical Engineers No. 02-26.

European Search Report dated Aug. 7, 2014, issued in connection with related EP14164658.

Extended Search Report dated Aug. 26, 2014, issued in connection with related EP14164658.

Non-Final Rejection Office Action dated Aug. 27, 2014, in connection with related U.S. Appl. No. 14/175,813, filed Feb. 7, 2014.

Notice of Allowance date mailed Aug. 4, 2014 in connection with related U.S. Appl. No. 14/175,829, filed Feb. 7, 2014, Vivek Shenoy.

Office Action dated Dec. 19, 2014, in connection with U.S. Appl. No. 13/843,128, filed Mar. 15, 2013.

Response to Final Office Action dated Apr. 1, 2013, in connection with related U.S. Appl. No. 13/002,829, filed Aug. 27, 2009.

Response to First Non-Final Office Action dated May 5, 2014, in connection with related U.S. Appl. No. 14/175,829, filed Feb. 7, 2014.

Response to Restriction Requirement dated Oct. 27, 2014, issued in connection with related U.S. Appl. No. 13/843,128, filed Mar. 15, 2013.

Restriction Requirement dated Aug. 25, 2014, issued in connection with related U.S. Appl. No. 13/843,128, filed Mar. 15, 2013.

International Search Report and Written Opinion dated Jul. 3, 2015, in connection with related PCT/US2015/019938, filed Mar. 11, 2015.

Office Action dated Jul. 1, 2015, in connection with related U.S. Appl. No. 13/974,930, filed Aug. 23, 2013.

Restriction Requirement dated Jul. 23, 2015, in connection with related U.S. Appl. No. 14/642,121, filed Mar. 9, 2015.

Response to First Non-Final Office Action dated Nov. 2, 2015, in connection with U.S. Appl. No. 13/974,930, filed Aug. 23, 2013.

Non-Final Office Action dated Oct. 7, 2015, in connection with U.S. Appl. No. 14/642,121, filed Mar. 9, 2015.

Gumpel et al., An Objective Assessment of Synovitis of the Knee: Measurement of the Size of the Suprapatellar Pouch on Xeroradiography. Annals of the Rheumatic Diseases. 1980, (39): 359-366.

Response to First Non-Final Office Action dated Jan. 25, 2016, in connection with related U.S. Appl. No. 14/642,121, filed Mar. 9, 2015.

Office Action dated Feb. 26, 2016, in connection with related U.S. Appl. No. 13/974,930, filed Aug. 23, 2013.

Appellant's Brief dated Mar. 15, 2016, in connection with related U.S. Appl. No. 13/002,829, filed Jan. 6, 2011.

Response to Final Office Action dated Aug. 10, 2015, in connection with related U.S. Appl. No. 13/843,128, filed Mar. 15, 2013.

Response to Restriction Requirement dated Sep. 23, 2015, in connection with related U.S. Appl. No. 14/642,121, filed Mar. 9, 2015.

Supplemental Response to Final Office Action dated Sep. 3, 2015, in connection with related U.S. Appl. No. 13/843,128, filed Mar. 15, 2013.

Final Office Action dated Sep. 15, 2015, in connection with related U.S. Appl. No. 13/002,829, filed Jan. 6, 2011.

Chow, S. P. et al., Fracture of the Tibial Tubercle in the Adolescent; British Editorial Society of Bone and Joint Surgery, vol. 72-B. No. 2, Mar. 1990.

(56) References Cited

OTHER PUBLICATIONS

Lafaver, et al., "Tibial Tuberosity Advancement for Stabilization of the Canine Cranial Cruciate Ligament-Deficient Stifle Joint: Surgical Technique, Early Results, and Complications in 101 Dogs", Veterinary Surgery, 36:573-586, 2007.
Office Action dated May 5, 2016, in connection with U.S. Appl. No. 14/542,121, filed Mar. 9, 2015, Shenoy.

* cited by examiner

APPARATUS AND METHODS FOR TREATMENT OF PATELLOFEMORAL CONDITIONS

RELATED APPLICATION DATA

This application claims the benefit of priority of U.S. Provisional Patent Application Ser. No. 61/951,469, filed Mar. 11, 2014, and U.S. Provisional Patent Application Ser. No. 61/951,470, filed Mar. 11, 2014, both of which are entitled "Apparatus and Methods for Treatment of Patellofemoral Conditions"; this application is also a continuation-in-part of U.S. Nonprovisional patent application Ser. No. 13/002,829, filed Aug. 27, 2010, and titled "Method and Apparatus for Force Redistribution in Articular Joints"; which application is a 371 of International Patent Application No. PCT/US10/46996, filed Aug. 27, 2010, and titled "Method and Apparatus for Force Redistribution in Articular Joints", which claims the benefit of priority of U.S. Provisional Patent Application Ser. No. 61/237,518, filed Aug. 27, 2009, and U.S. Provisional Patent Application Ser. No. 61/288,692, filed Dec. 21, 2009, each entitled "Method and Apparatus for Force Redistribution in Articular Joints"; this application is also a continuation-in-part of U.S. Nonprovisional patent application Ser. No. 13/843,128, filed Mar. 15, 2013, and titled "Method and Apparatus for Altering Biomechanics of Articular Joints"; which application claims priority to U.S. Provisional Patent Application Ser. No. 61/620,756 filed on Apr. 5, 2012 and U.S. Provisional Patent Application Ser. No. 61/695,406 filed on Aug. 31, 2012; and which application is also a continuation-in-part of U.S. Nonprovisional patent application Ser. No. 12/870,462, filed on Aug. 27, 2010 (now U.S. Pat. No. 8,597,362 issued Dec. 3, 2013), which claims priority to U.S. Provisional Patent Application Ser. No. 61/237,518, filed Aug. 27, 2009, and U.S. Provisional Patent Application Ser. No. 61/288,692, filed Dec. 21, 2009. Each of the foregoing applications is incorporated by reference herein in its entirety.

The present invention generally relates to the field of orthopedic prostheses and procedures. In particular, the present invention is directed to apparatus and methods for treatment of patellofemoral conditions.

BACKGROUND

As the present invention is directed to apparatus and methods for treatment of patellofemoral conditions, a basic discussion of the anatomy of the knee with a focus on the patellofemoral structures may assist in describing the various embodiments of the invention. FIG. 1 is a schematic portrayal in side view of a human knee. The bones of the knee joint comprise the femur (F), tibia (T), and patella (P). The fibula (fib) is another bone in the lower leg that attaches to the tibia. As primarily relevant to embodiments of the present invention, connective tissues of the knee joint include the patellar tendon (PT) and the quadriceps tendon (QT). The patellar tendon is also referred to as the patellar ligament as its primary function is to create a connection between bones, i.e., the tibia and patella. The patellar tendon extends from the caudal (lower) extent of the patella to an attachment point on the tibial tuberosity (TT) of the tibia. The tibial tuberosity comprises a raised area on the anterior (forward) aspect of the tibia, caudally positioned (toward the foot or lower) with respect to the cranial (upper) end of the tibia. The quadriceps tendon extends from the cranial extent of the patella and joins with the quadriceps-femoris muscle.

The knee is a synovial joint, meaning that the bones are not directly joined but are surrounded by dense connective tissues forming an articular capsule (C) lined by a synovial membrane. The capsule defines a synovial cavity or intracapsular space (IC) that contains the articular cartilage of the joint (not shown) and synovial fluid that acts to reduce friction between the articular cartilages. The approximate extent of the capsule is indicated in FIG. 1 by dashed lines (C'). The quadriceps and patellar tendons lie outside the capsule. Also outside the capsule is the infrapatellar fat pad (FP). The fat pad is situated posteriorly and caudally with respect to the patella and joins with the patellar tendon on its posterior side over much of its length. The knee joint also includes a number of bursae to protect and facilitate movement between various bony and soft tissues. One of these bursae is the deep infrapatellar bursa (B), which allows for movement of the patellar tendon over the tibia. This bursa is positioned between the upper part of the tibia and the patellar tendon and lies in a pocket outside of the infrapatellar fat pad.

Because of the importance of the capsule in protecting and lubricating the articular cartilage, it is usually preferable, whenever possible in a knee intervention, to avoid penetrating the capsule. Because of the role of the infrapatellar fat pad in protecting the knee, it is also usually preferable to avoid dissecting the fat pad during knee interventions. Previously, removal of all or part of the fat pad was common in arthroscopic procedures in order to permit better visibility for the surgeon. However, it has been discovered that damage to the fat pad can lead to scarring, which can be painful and even crippling in some patients.

Treatments for various patellofemoral pathologies such as patellofemoral pain and patellofemoral osteoarthritis (PFOA) have been increasingly investigated. One early treatment, which involves anteriorization of the patellar tendon by a relatively invasive surgical procedure, was devised by Dr. Paul Maquet in the early 1960s. See, P. Maquet, 30 Revue Du Rhumatisme, No. 12, December 1963, pp. 779-783, "Biomechanical Treatment of Patellofemoral Osteoarthritis, Advancement of the Patellar Tendon" (translated title). In this procedure, an iliac bone autograft is implanted under the patellar tendon to relieve pressure in the patellofemoral space. Later Dr. Maquet evolved his technique to cut the tibial tuberosity away from the tibia and reposition it. This became known as the Maquet Osteotomy, which has been performed on tens of thousands of patients over the years with positive results. See, e.g, Maquet, Biomechanics of the Knee, pp. 134-143 (pub. Springer-Verlag 1976). However, the Maquet Osteotomy is a highly invasive procedure, which carries with it all of the risks and costs associated with highly invasive orthopedic surgeries.

FIG. 2 is a schematic illustration of a relatively square bone implant 2 of the type proposed by Dr. Maquet implanted on the tibia (T) under the patellar tendon (PT). The patellar tendon is attached cranially to a caudal portion of the patella, and caudally to the tibia at the Tibial Tuberosity (TT). The natural line of action of the patella tendon would be generally along a line (L) extending between the two attachment points. Placing the bone implant 2 under the patellar tendon moves the patellar tendon anteriorly between its two attachment points and thus alters the line of action with respect to the patella. The new line of action ($L_1$), oriented more away from the patellofemoral space can reduce the pressure on that space. Said another way, anteriorizing the patellar tendon renders the angle between the patellar tendon and the quadriceps tendon more obtuse, reducing the resultant force pressing the patella against the femur.

However, the success of such a procedure may depend heavily on the configuration of the implant used. If the anterior, tissue-engaging surface of the implant is roughly perpendicular to the caudal face of the implant and/or parallel to the underlying surface of the tibia, it displaces the patellar tendon relatively directly anteriorly (perpendicular to the tibial surface) and creates an abrupt step at the caudal edge of the implant, which can produce a number of complications. First is the creation of an unsightly bump on the knee. This is not merely a cosmetic problem, as the bump may catch on clothing or other, harder objects that could cause bruising or injury in the course of daily activity. Second, such an implant could be extremely uncomfortable in certain common positions. For example, if a patient with such an implant were to kneel on that knee, all of the load would be placed on that implant, which could be painful and also damaging to the patellar tendon.

A third possible complication arises from the fact that an implant shaped such as implant 2 also pulls the patella caudally, creating an undesirable misalignment. This condition is referred to as "Patella Infera" or "Patella Baja". The symptoms of this misalignment can include pain on quadriceps contraction, inadequate quadriceps contraction, swelling, edema, joint stiffness, limited joint motion and limited patellar mobility.

Further, it may be desirable to maximize the area of the posterior surface of the implant that lies against the bone in order to spread the forces on the implant over as wide an area as possible. And, in order to minimize Patella Baja, it may be desirable to engage the patellar tendon as far cranially as possible without interfering with the patella or other tissues during knee movement. Yet, the space in which the implant is to be located, between the tibial tuberosity and the fat pad, bursa, and/or capsular tissues, is extremely limited. If the posterior surface of the implant extends too far cranially along the bone surface it may interfere with the fat pad, bursa, or joint capsule, causing pain or other complications. What is needed, therefore, are devices and methods for relieving patella-femoral pain due to osteoarthritis or other conditions that overcome the foregoing challenges.

SUMMARY OF THE DISCLOSURE

In one implementation, the present disclosure is directed to a prosthesis for treating disorders of the knee in the patellofemoral compartment of the knee. The prosthesis includes a fixation portion configured to be mounted to the tibia proximate the upper tibial extremity and medially or laterally of the tibial tuberosity, a spanning section configured and dimensioned to extend cranially and laterally or medially from the fixation portion in a direction towards the tibial mid-line, and a displacement portion configured and dimensioned to (i) extend from the spanning section further laterally or medially under patellar tendon and in engagement therewith, and (ii) displace the patellar tendon anteriorly sufficiently to alter the location, angle or magnitude of forces exerted thereby on the patella so as to achieve a therapeutic effect in patellofemoral compartment of the knee.

In another implementation, the present disclosure is directed to a prosthesis for treating disorders of the knee in the patellofemoral compartment of the knee. The prosthesis includes a fixation portion configured to be mounted to the tibia proximate the upper tibial extremity and medially or laterally of the tibial tuberosity, a spanning section configured and dimensioned to extend cranially and laterally or medially from the fixation portion in a direction towards the tibial mid-line, a displacement portion configured and dimensioned to extend from the spanning section further laterally or medially under the patellar tendon, defining a space between at least a part of the displacement portion and tibial surface, to displace the patellar tendon at least anteriorly from a normal, anatomical path; and a supplemental support element with a bone engaging surface disposed at an end of the displacement portion opposite the spanning section, the displacement portion being further configured and dimensioned to dispose the bone engaging surface against the tibial surface when the fixation portion is mounted to the tibia.

In yet another implementation, the present disclosure is directed to a prosthesis for repositioning a target tissue, the target tissue comprising a connective tissue or muscle relative to a bone on which the target tissue acts. The prosthesis includes a fixation portion having one or more fixation features configured to receive fixation elements for securing the implant to the bone, and a displacement portion having a first end connected to the fixation portion and a free end opposite the first end, the displacement portion having a bearing surface configured to atraumatically engage and reposition the target tissue relative to the bone wherein the displacement portion has a base portion configured to engage the bone and a cantilevered portion extending from the base portion to the free end, the cantilevered portion being configured to be spaced apart from bone when the base portion is engaging the bone.

In still another implementation, the present disclosure is directed to a femorally mountable prosthesis for treating patellofemoral osteoarthritis or patellar maltracking. The prosthesis includes a fixation portion including one or more fixation holes, the fixation portion being generally straight and elongated, and configured for fixation to the femur at least approximately aligned with the femoral shaft on a lateral, medial or anterior-medial/lateral side of the femur, and cranially with respect to the patella; a displacement portion configured and dimensioned to (i) be positioned under the quadriceps tendon cranially with respect the attachment point of the quadriceps tendon to the patella, and (ii) to atraumatically engage and displace the quadriceps tendon anteriorly relative to the femur to increase space in the patellofemoral area; and a spanning section interconnecting the fixation portion and the displacement portion, the spanning section configured and dimensioned to position the displacement portion to engage and displace the quadriceps tendon.

In still yet another implementation, the present disclosure is directed to an instrument for reshaping a bone surface. The instrument includes a shaft having proximal and distal ends arranged along a longitudinal axis and an elongated file element coupled to the distal end of the shaft and extending in a direction transverse to the shaft and longitudinal axis, the file element having a curvature about a second axis transverse to the longitudinal axis and having anterior and posterior surfaces lying in respective planes intersected by the second axis, at least one of the anterior and posterior surfaces having features configured to reshape bone when the file is moved in engagement therewith.

In another implementation, the present disclosure is directed to a method for treating patellofemoral osteoarthritis or patellar maltracking. The method includes mounting a prosthesis on the tibia at a fixation site outside of the knee joint capsule proximate the upper tibial extremity and medially or laterally of the tibial tuberosity without rupturing the capsule and with a portion of the prosthesis extending under the patellar tendon to displace the patellar tendon from a normal, anatomical path in at least an anterior direction and without disrupting the attachment of the infrapatellar fat pad to the tibia and without dissecting the infrapatellar fat pad.

In yet another implementation, the present disclosure is directed to a method of implanting a device on the tibia. The method includes inserting a file element through an incision on a medial or lateral side of the tibia such that the file element extends in a medial-lateral direction across an anterior surface of the tibia cranially of the tibial tuberosity and a handle coupled to the file element extends in a cranial-caudal direction along the tibia outside the incision; moving the handle such that file element reshapes the anterior surface of the tibia to a first shape; placing an implant through the incision and positioning a base portion of the implant in engagement with the anterior surface of the tibia with a displacement portion of the implant under the patellar tendon, the base portion having a posterior surface with a shape complementary to the first shape; and securing the implant to the tibia.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein:

FIGS. 8A, 8B and 8C show alternative embodiments, wherein FIG. 8A is a schematic illustration of an implant on the tibia, FIG. 8B is a perspective view of the implant, and FIG. 8C illustrates a further alternative, as would be seen along line C-C in FIG. 8B;

FIGS. 9A and 9B show further alternative embodiments, wherein FIG. 9A is a schematic illustration of the implant on the tibia and FIG. 9B is a cross-sectional view through section A-A of FIG. 9A;

FIG. 9C illustrates another alternative embodiment, again in a view through section A-A of FIG. 9A;

DETAILED DESCRIPTION

Embodiments of the present invention employ an improved implant geometry with an appropriately curved cross-section to address drawbacks of some prior devices and procedures, such as an unsightly and uncomfortable bump, concerns about tissue damage, and the caudal movement of the patella as previously discussed. Other embodiments of the present invention employ supplemental support/fixation means and specially shaped fixation portions to facilitate implantation, increase fixation security and resist torqueing forces. Further embodiments of the present invention encompass less invasive methods for treatment of patellofemoral conditions, including employing implant embodiments disclosed herein.

The present inventors have disclosed implants for treating PFOA in United States Patent Publication US 2011/0213466, entitled "METHOD AND APPARATUS FOR FORCE REDISTRIBUTION IN ARTICULAR JOINTS," and, more recently in United States Patent Publication US 2013/0211521, entitled "METHOD AND APPARATUS FOR ALTERING BIOMECHANICS OF ARTICULAR JOINTS," each of which is incorporated herein by reference in their entirety. In certain embodiments therein disclosed, an implant portion is inserted underneath the patellar tendon, just cranial to the attachment of the patellar tendon to the tibial tuberosity. This implant portion displaces the patellar tendon anteriorly, flattening the angle between the patellar tendon and the quadriceps tendon. This change in angle reduces the resultant pressure of the patella against the femur, reducing patellar pain and patellofemoral cartilage wear. The implant may also improve patellar tracking, or shift the location, angle or loading of the patella against the femur.

Figures 2, 3:
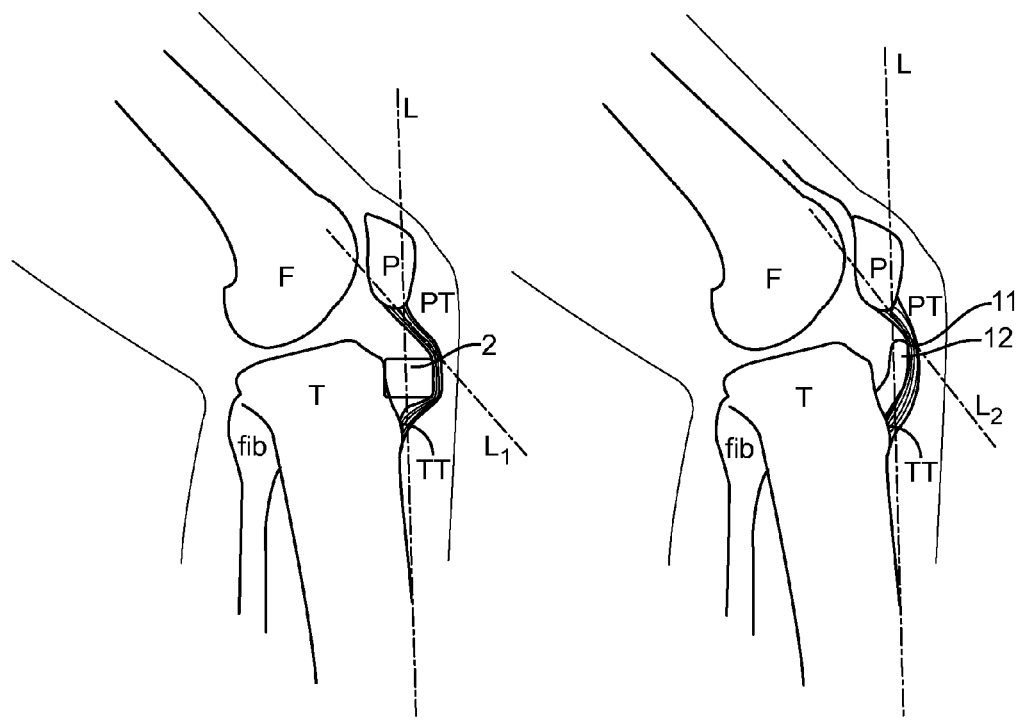
FIG. 2 is a schematic representation of an implant in accordance with early work of Dr. Paul Maquet.
FIG. 3 is a schematic illustration of an implant according to one disclosed embodiment.

FIG. 3 schematically illustrates features of the embodiments in this disclosure. The schematic side view of FIG. 3 helps to illustrate the positioning and curved shape of the bearing surface 11 and displacement portion 12 of embodiments disclosed herein. The bearing surface 11 is the surface of the displacement portion 12 in contact with the patellar tendon. Line $L_2$ shows the approximate line of action of the patellar tendon after repositioning over displacement portion 12. To simplify FIG. 3 for discussion purposes, fixation means and other implant structures such as the fixation portion and spanning section discussed in more detail below are not called out. The various fixation and support structures discussed below facilitate the cantilevering of displacement portion to better accommodate soft tissue structures while properly positioning the bearing surface as discussed in more detail below.

In general, implants according to embodiments of the invention will be configured and dimensioned to displace the tissue targeted for treatment by between about 5 mm to about 30 mm from the natural, anatomical tissue path. In some embodiments, the displacement will be greater than about 10 mm. Overall displacement amounts can be set through a combination of shape and size of the fixation portion, spanning section and displacement portion of the implant as previously described. Working within those parameters, it has been discovered that by shaping the bearing surface at least approximately as a quarter-circle in cross-section with a minimum radius of about 8 mm, caudal biasing of the patella can be reduced. Further flattening the curvature of the bearing surface, by increasing radius, or making the surface more oval, elliptical, hyperbolic, or of another complex shape, can further reduce caudal biasing, but space limitation arising from the anatomy and need for a minimum displacement to achieve therapeutic effects may limit the amount of such flattening that may be applied to the implant. In addition, the displacement portion and/or bearing surface may be shaped and dimensioned to provide different magnitudes of displacement at different points along the surface such that the tissue is displaced different amounts at different joint positions, e.g. at different points in the gait cycle. As used herein, "therapeutic effect" means an effect on a treated joint that reduces forces acting on the articular surfaces, reduces wear, lessens pain or provides another positive outcome for the patient whether across the joint as a whole or in particular compartments of the knee. "Therapeutic effect," however, does not imply, and should not be understood as requiring, any specific, quantified outcome other than as stated above.

Figure 4A:
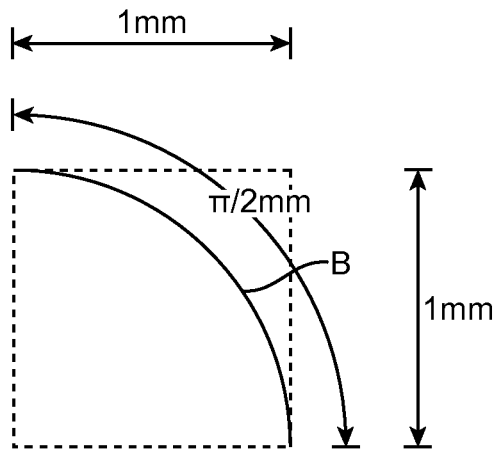
FIGS. 4A and 4B are diagrams illustrating profiles for tissue bearing surfaces in accordance with disclosed embodiments.
Figure 4B:
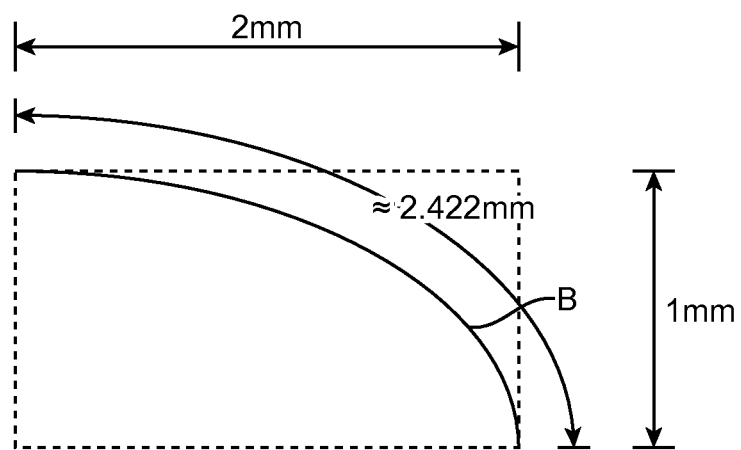

As shown in FIG. 4A, for a bearing surface (B) with a depth and length of 1 mm in each dimension, the patella is pulled caudally by only about ($\Pi/2-1$) or 0.57 millimeters. In an alternative embodiment, the bearing surface curve may be flattened even further with a length of about 2 mm while maintaining the 1 mm depth, as shown in FIG. 4B. In this embodiment, the caudal displacement of the patella would be less than half of the anterior displacement. The generally elliptical shape of the bearing surface causes such an implant to extend generally twice as far cranially as it does anteriorly and thus would pull the patella caudally by an amount approximately equal to 0.42 times the anterior displacement. Caudal displacement with an elliptically shaped bearing surface may be estimated based on a corresponding elliptical circumference. For example, using an "ellipse calculator" (e.g. as available online at http://www.cleavebooks.co.uk/scol/callipse.htm) and selecting a major axis of 4 and a minor axis of 2, a circumference of 9.69 can be determined. Dividing the circumference by 4 gives 2.422 (approximately one quarter of the elliptical circumference corresponding to the overall length of the bearing surface). With this information, it may be estimated that a curved bearing surface with a cranial-caudal length of 2 cm and an anteriorization of 1 cm will pull the patellar tendon caudally approximately 0.42 cm.

A geometry as described in the preceding paragraphs should dramatically reduce the complications caused by patella baja from square or steeply profiled implants. For example, a prior art implant with a square cross-section, such as shown in FIG. 2, would pull the patella caudally by approximately one millimeter for each millimeter of anteriorization; about twice the amount of caudal displacement created by embodiments disclosed herein for the same amount of anteriorization.

In certain embodiments, the bearing surface 11 will be positioned with its outer most point (apogee) at a perpendicular distance from the surface of the tibia below it of about 0.3-3 cm, or more typically about 0.5-1.5 cm for an implant configured to treat an average adult knee. The width of the bearing surface in the generally cranial-caudal direction will be about 0.5-3.0 cm, or more typically about 1.0-2.5 cm. While distance from the tibia to the apogee of the bearing surface can equal the bearing surface width, in some embodiments the width will be greater than that distance, about 1.1-3.0 times greater, or more typically about 1.5-2.0 times greater. Further alternative embodiments may employ bearing surfaces with compound curvatures comprising elements of FIGS. 4A and 4B as previously discussed.

Figure 3A:
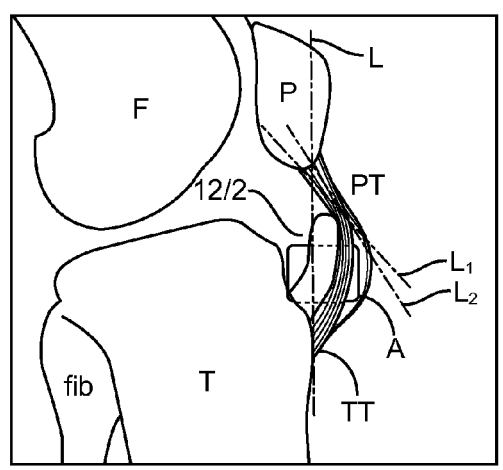
FIG. 3A is a combined view with the embodiment shown in FIG. 3 superimposed over the implant shown in FIG. 2.

A further physiologic benefit to an implant with the curved geometry as described is that the forces pressing the patella against the femur are highest when the knee is bent, such as when a person is climbing stairs. As shown in FIG. 3A, where an embodiment of the present invention is superimposed over a prior implant, the shape of the present invention is more effective in flattening the angle between the patellar tendon and the quadriceps tendon when the knee is bent. It also reduces the focal stress on the sharply angled portion of the patellar tendon caused by such prior implants, especially when the leg is straight. The extreme caudal positioning of the prior implant 2 is indicated at (A) in FIG. 3A.

Figure 5A:
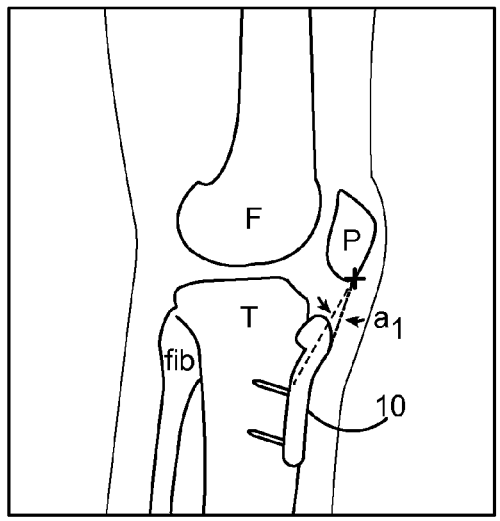
FIGS. 5A, 5B and 5C are a series of schematic illustrations showing disclosed embodiments implanted on the tibia at the knee, with the knee at flexion angles of about 0°, 45° and 90°, respectively.
Figure 5B:
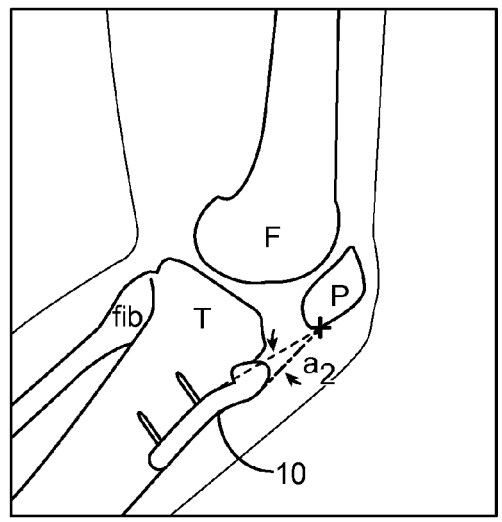
Figure 5C:
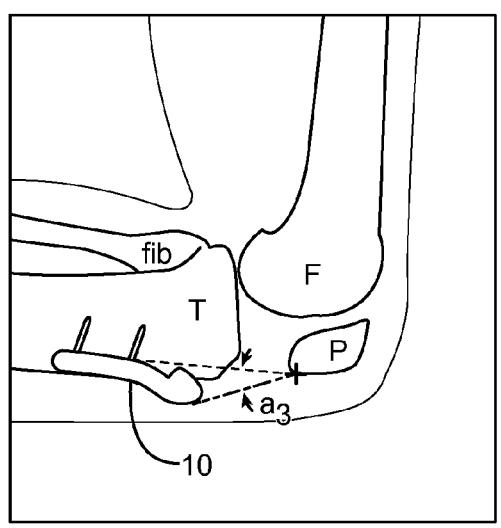

The beneficial effect of embodiments of the present invention as related to knee flexion are further illustrated in FIGS. 5A-C. From these figures, it can be seen that the angle α of anteriorization is increased from the natural line of the patella tendon from $\alpha_1$ with the knee fully extended, to $\alpha_2$ at partial flexion, up to $\alpha_3$ at 90° flexion in FIG. 5C, where $\alpha_1 < \alpha_2 < \alpha_3$. The unloading provided by the implant thus increases with knee flexion, providing the greatest relief when the patella is maximally loaded.

Figure 6A:
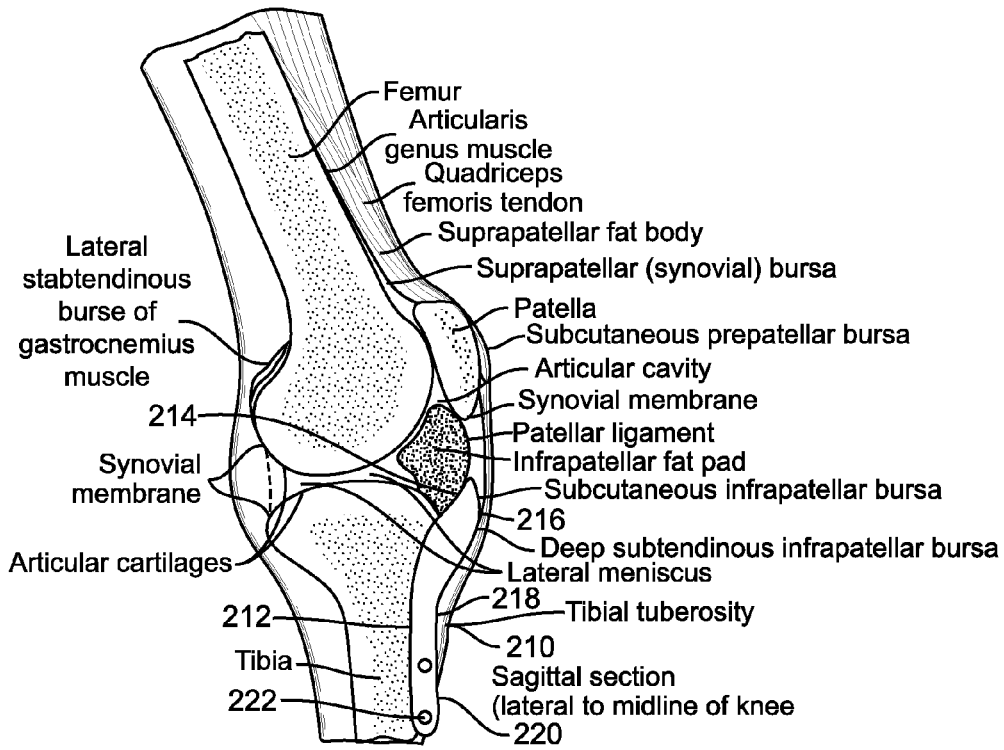
FIGS. 6A and 6B illustrate another embodiment disclosed by the inventors in an incorporated application.
Figure 6B:
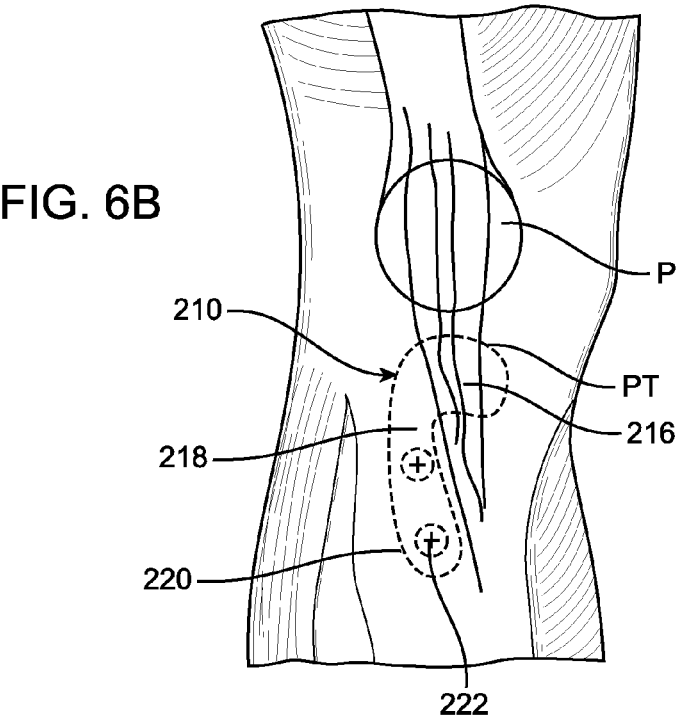

Further embodiments are shown in FIGS. 6A and 6B (corresponding to FIGS. 24 and 25, respectively, of the present inventors' first incorporated publication above), and FIGS. 7A-F (corresponding to FIGS. 8 and 9A-E, respectively, of the present inventors' second incorporated publication above). In the embodiments of FIGS. 6A and 6B, implant 210 includes a support member 212 and bearing member 214. The support and bearing members are functionally divided into displacement portion 216, spanning section 218 and fixation portion 220. The displacement portion, with the bearing member is partly cantilevered over the tibia so that a portion of the fat pad may be received thereunder.

FIGS. 7A-G depict an exemplary prototype of implant 300 for treating patellofemoral osteoarthritis and/or patellar maltracking for the right knee. Implant 300 has a fixation portion 312 having one or more holes 315 for receiving screws for anchoring the implant to bone. Fixation portion 312 is generally straight and elongated, being configured for positioning in general alignment with the tibial shaft on the medial or anterior-medial side of the tibia. Bone engaging surface 313 is provided on the bone facing side of the fixation portion. Holes 315 are preferably positioned in approximate alignment with a longitudinal centerline of fixation portion 312.

Displacement portion 314, is configured and dimensioned to be positioned under the patellar tendon caudally separated from the insertion point of the tendon in the tibia. The displacement portion 314 is configured to atraumatically engage the tendon and displace it anteriorly relative to the tibia. The displacement portion 314 has a length in the lateral-medial direction generally selected to accommodate the full width of the tendon so that the tendon remains engaged along its entire width as it slides on the displacement portion. Displacement portion 314 preferably has a convex curvature on its outer tissue-engaging surface (bearing surface 309), preferably being curved at least around an axis generally parallel to the tibial shaft, usually being curved also around an axis perpendicular to the tibial shaft, and more preferably being spherical or partially spherical. Displacement portion 314 has a width in the caudal-cranial direction is selected so that it does not interfere with the patella or engage the insertion point of the tendon, typically being less than its length. A spanning section 316 interconnects fixation portion 312 and displacement portion 314. Spanning section 316, in the embodiment illustrated, extends cranially and laterally from fixation portion 312 to displacement portion 314, forming a curve of about 90° about a dorsal-ventral axis. Where fixation portion 312 is configured for attachment to a more medial aspect of the tibia, spanning section 316 will extend ventrally as well as cranially and laterally from fixation portion 312, preferably being curved about an axis generally parallel to the tibial shaft. Displacement portion 314 appropriately displaces the patellar tendon in cooperation with the fixation portion 312 and spanning section 316.

Displacement of the target tissue can be altered by changing the length, curvature and angle of the spanning section among other features. For example, the angle α between the displacement portion 314 and the fixation portion 312 (as measured at the intersection of the center line axes of the two portions in the top view of the implant in FIG. 7B) may range from about 80 degrees to 135 degrees, more specifically from about 85 degrees to 120 degrees, and in some embodiments about 90 degrees to 110 degrees.

The width $W_1$ of the fixation portion 312 (FIG. 7C) typically will be large enough to span a substantial portion of the width of the tibia and to accommodate one or more screw holes of sufficient size, ranging from about 10 mm to 25 mm. In some embodiments, width $W_1$ may be about 12 mm to 20 mm, and in other embodiments about 14 mm to 18 mm. The length $L_1$ of the fixation portion 312 will be selected to accommodate a sufficient number of screw holes in the cranial-caudal direction along the tibia, usually at least two and in some embodiments up to five or more, and may range from about 20 mm to 50 mm, more specifically about 25 mm to 45 mm, and in some embodiments about 30 mm to 40 mm.

The width $W_2$ (generally cranial-caudal direction) of the displacement portion 314 (FIG. 7B) is generally selected to provide a broad area of contact with the tendon to spread the force and reduce wear, while not interfering with the patella or the tendon insertion point throughout the full range of joint motion. Width $W_2$ may thus range from about 10 mm to 25 mm, more specifically about 12 mm to 20 mm, and in some embodiments about 14 mm to 18 mm. The length $L_2$ (generally medial-lateral direction) of the displacement portion 314 is selected so that the displacement portion extends under the full width of the tendon so that the entire width of the tendon remains in engagement and displaced the desired amount throughout the range of joint motion. Length $L_2$ may thus range from about 20 mm to 50 mm, more specifically about 25 mm to 45 mm, and in certain embodiments about 30 mm to 40 mm.

Figure 7A:
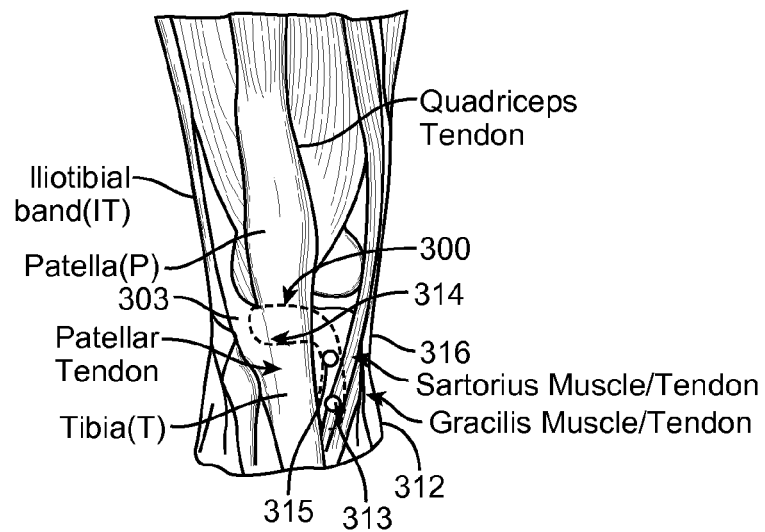
FIGS. 7A, 7B, 7C, 7D, 7E, 7F and 7G illustrate features of another embodiment disclosed by the present inventors in another incorporated application.
Figure 7B:
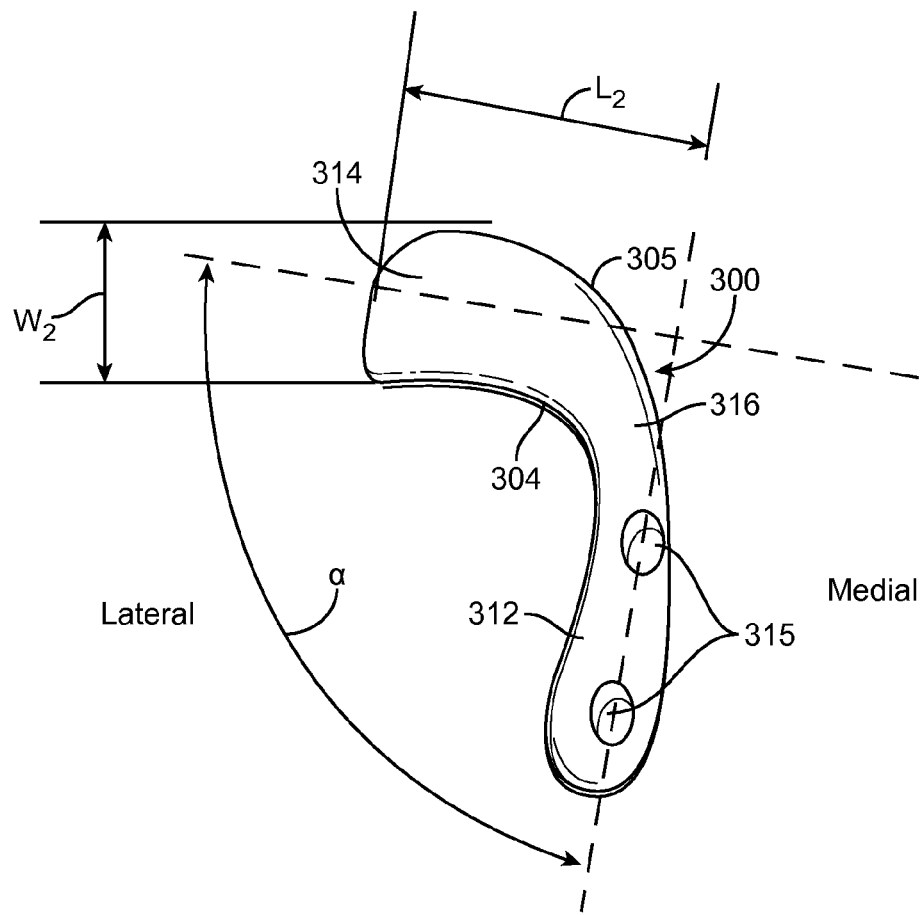
Figure 7C:
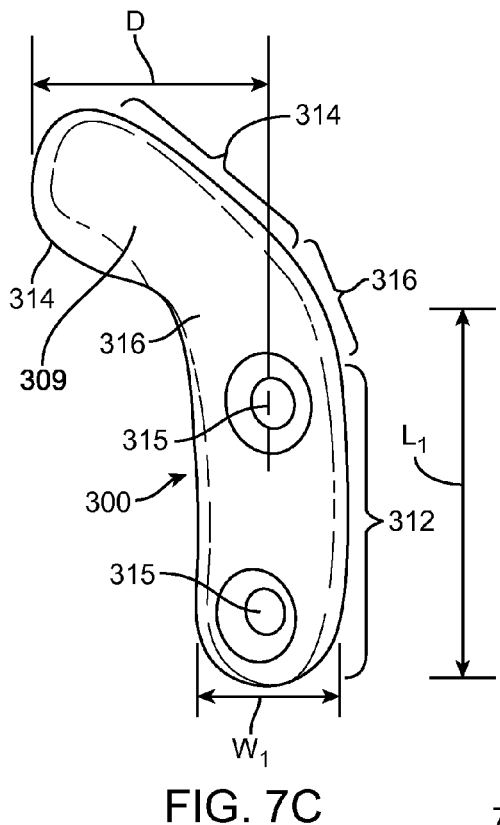
Figure 7D:
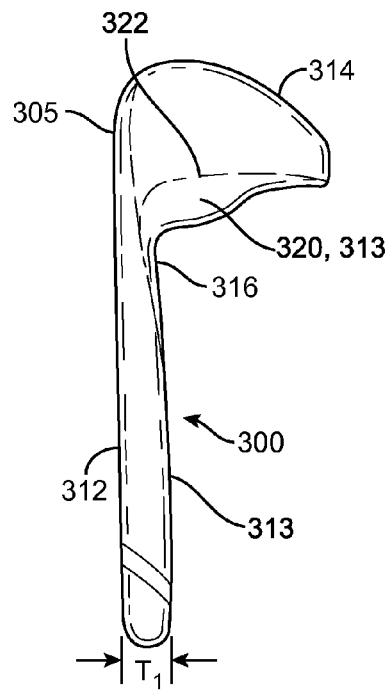
Figure 7F:
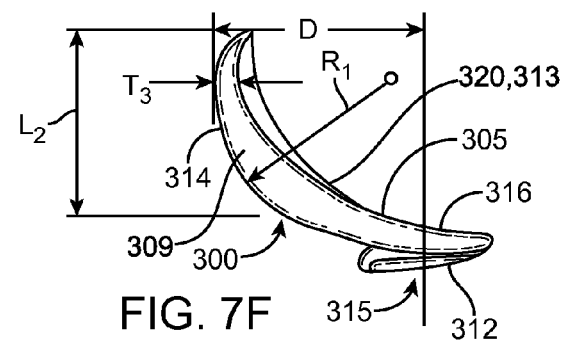
Figure 7E:
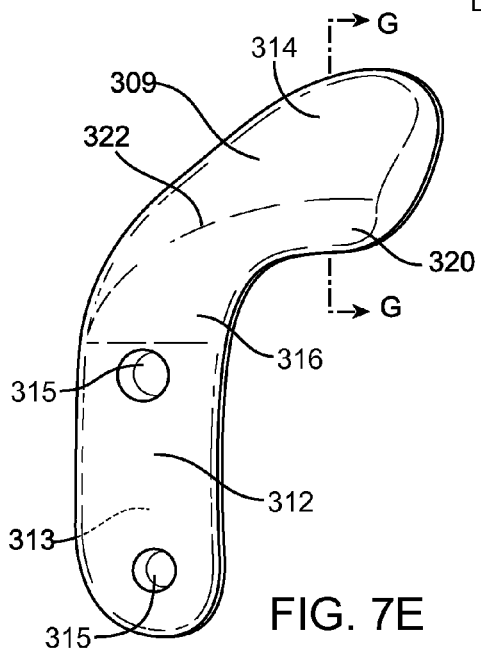
Figure 7G:
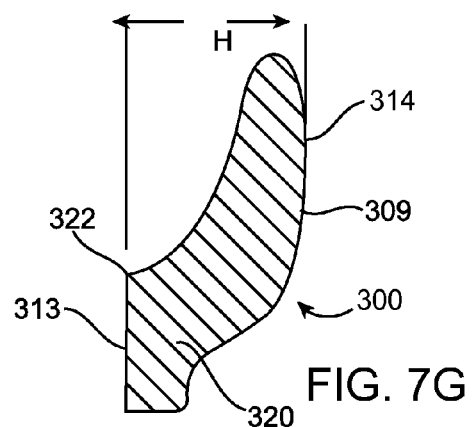

As best seen in FIGS. 7E-G, implant 300 also includes a supporting section 320 extending along the caudal extent of displacement portion 314, into spanning section 316 and merging into the bone engaging surface 313 of fixation portion 312. As will be appreciated by persons of ordinary skill, contour line 322 illustrates the approximate extent of supporting section 320 from the displacement portion, through the spanning section and into the fixation portion.

Supporting section 320 rests on the surface of tibia between the tendon insertion point and the fat pad and/or capsular tissue. The cranial-caudal length of bone engaging surface 313, i.e., the approximate distance from cranial most location of contour line 322 delineating the cranial extent of the supporting section, to the caudal end of fixation portion 312 is preferably greater than the distance from same point on contour line 322 to the cranial edge of displacement portion 314. The appropriate distance ratios between these two regions increases the moment arm resisting torqueing force applied by the patellar tendon through the cantilevered displacement portion 314 to help fix the implant in place and resist loosening over time due to the cyclic torqueing forces applied by knee flexion and extension.

Displacement portion Height (H), shown in FIG. 7G, is the perpendicular distance from the apogee of bearing surface 309 to the bone engaging surface 313. Height (H) directly effects the amount of displacement of the tendon achievable with the implant. In general terms, the displacement distance will approximately equal Height (H) minus the normal anatomical distance between the patellar tendon and the tibial surface below it at the location of the displacement portion when implanted.

Implant depth D, along with the radius of curvature $R_1$ of the outer surface of displacement portion 314, shown in FIG. 7F, are selected to balance tendon displacement throughout the range of joint motion with the appropriate fixation location. Radius of curvature $R_1$ is usually 20-35 mm, more preferably 22-33 mm, and most preferably 25-30 mm. For average patient anatomy, an overall implant depth (D), shown in FIGS. 7C and 7F, as measured from the outermost surface of displacement portion 314 to the centerline of the screw holes in fixation portion 312, would be in the range of 10-45 mm in order to provide target tissue displacements in the ranges cited hereinabove to achieve a therapeutic effect.

The inferior edge 304 of the spanning section 316 can also be curved to minimize or eliminate any contact with the medial edge of the patellar tendon. The superior surface edge 305 of the displacement portion 314 can be curved to allow for easy motion of the patellar tendon during flexion as well as to vary the displacement of the patellar tendon during flexion by varying the region of the implant surface in contact with the tendon at higher flexion angles. In one exemplary embodiment, implant 300 is placed on the medial side of the distal tibia such that fixation portion 312 is substantially aligned with the tibial shaft, the spanning section 316 is positioned to minimize contact with the medial edge of the patellar tendon, and the displacement portion 314, extending laterally from the spanning section, is substantially parallel to the tibial plateau.

A supporting section as generally described above may be incorporated into other embodiments disclosed herein to facilitate locating the fixation portion (and in particular bone screw site) at a distance from the area where displacement portion acts to allow for easier placement of the device, without a need to place fixation elements such as nails or screws under or close to the patellar tendon, the joint capsule or the infrapatellar fat pad. It also means that the displacement element can be appropriately rounded and smooth, without any surface roughness or disturbances due to fixation elements. And although the fixation portion is at a distance from the displacement portion, much of the force from the patellar tendon is transmitted through the supporting section directly onto the tibia behind it. Further, by extending the fixation portion 312 caudally down the tibia relative to the supporting section (and contour line 322), the leverage applied by the fixation screws is increased so as to counter any tendency of the displacement portion to be tilted toward the tibia under the forces exerted by the patellar tendon.

Figure 8A:
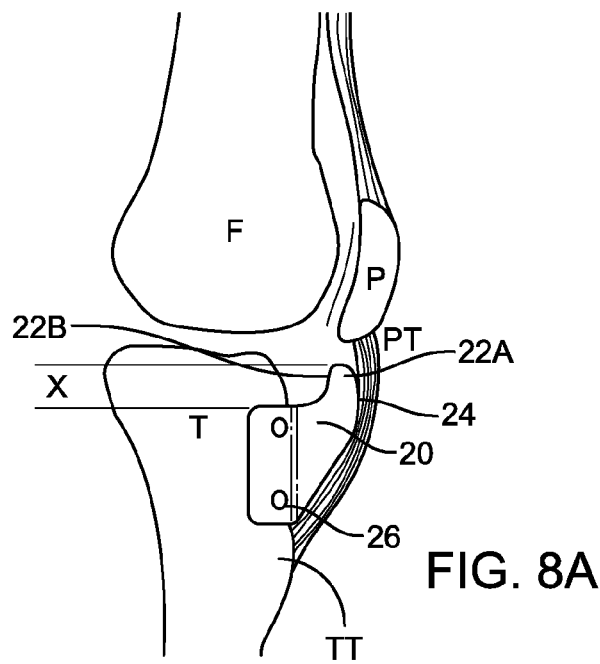
Figure 8B:
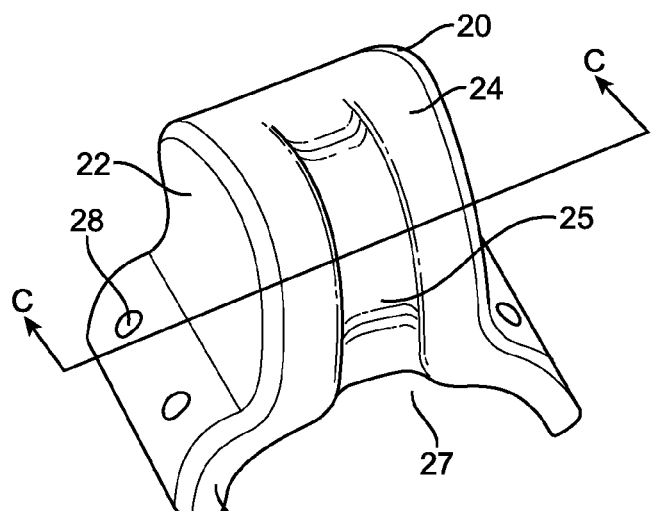

Another alternative embodiment of the present invention is shown in FIGS. 8A and 8B. While typically it would be preferable to position the fixation portion more caudally to locate the fixation means such as screws more distant from the joint capsule and other sensitive structures of the joint, in some patients and in some clinical situations this may not be possible, or fixation adjacent to the displacement portion may have other advantages. In this embodiment, implant 20 may have a displacement portion 22 with a bearing surface 24. The bearing surface may be curved as described above in connection with FIGS. 4A and 4B. The bearing surface also may be optionally provided with a concave groove or channel 25 extending in the cranial-caudal direction to assist in guiding the displaced tissue as it passes thereover. However, the same embodiment also may be provided without the channel. Implant 20 also may have a fixation portion 26 with a bottom surface having a slight concavity 27 in the cranial-caudal direction configured to be seated on the tibia just cranially of the tibial tuberosity. Fixation means 28 such as screw holes, spikes or bone ingrown facilitating elements may be included in fixation portion 26. Persons of ordinary skill in the art will appreciate that the features of the concave groove or channel 25 and/or bottom surface concavity 27 may be employed with other embodiments as described herein and are not restricted to use with implant 20.

As shown in FIG. 8A, and as employed by other embodiments of the invention disclosed herein, displacement portion 22 includes a cantilevered portion 22A extending in the cranial direction, forming an undercut region 22B on the inferior (bone facing) side of cantilevered portion 22A, cranially of fixation portion 26. Cantilevered region 22A is configured to extend cranially over the anterior surface of the tibia and the overlying fat pad such that the cranial edge of bearing surface 24 extends a distance X of about 5-30 mm, more preferably about 10-25 mm, and most preferably about 15-22 mm, from the cranial edge of fixation portion 26. This facilitates engagement of bearing surface 24 with the patellar tendon as far in the cranial direction as possible without interfering with the patella or femur, while undercut region 22B provides a space in which the fat pad, capsular ligaments or other soft tissues may reside. By engaging the patellar tendon further in the cranial direction, the displacement force applied to the patella has less of a caudal component, reducing "Patella Baja".

Figure 8C:
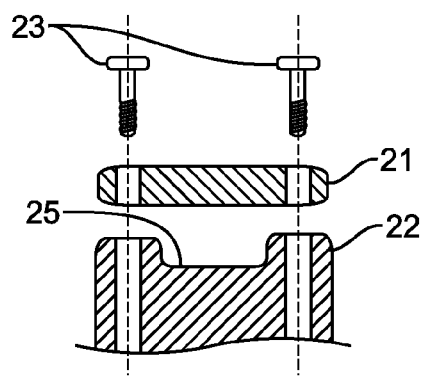

In another alternative, a cover member 21 may be provided as shown in FIG. 8C to protect and retain the tendon when it is received in channel 25. Cover 21 is securable over bearing surface 24, such as with screws 23.

Figure 9A:
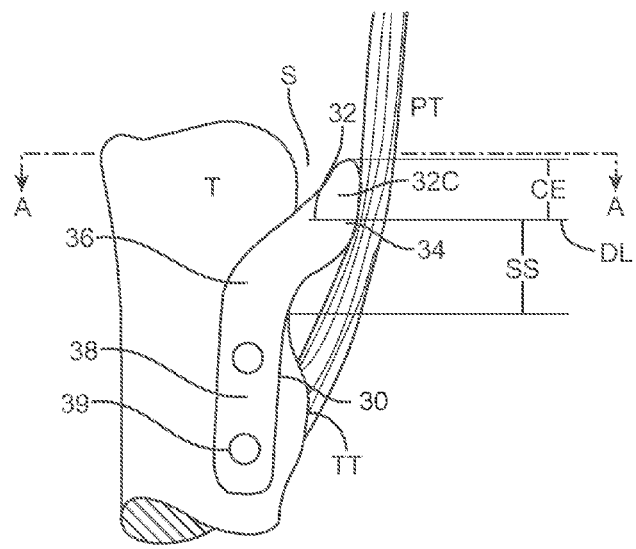
Figures 9B, 9C:
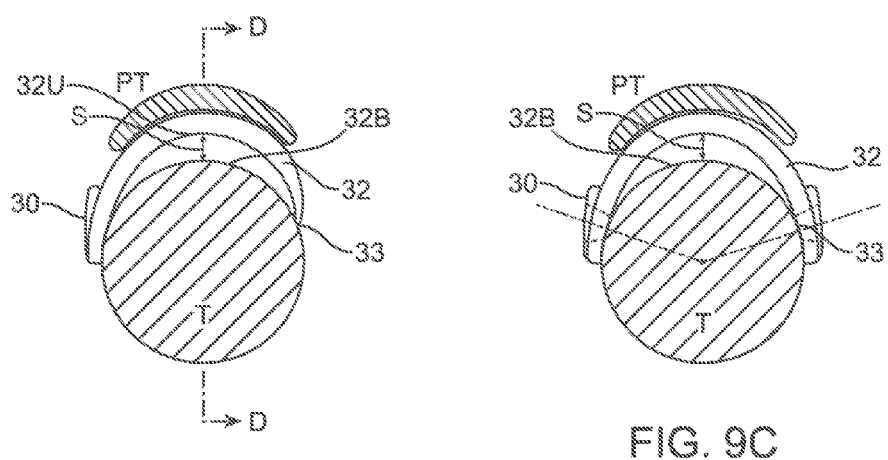

A further alternative embodiment of the present invention is shown in FIGS. 9A and 9B. In this embodiment, implant 30 may have a displacement portion 32 with a bearing surface 34. Bearing surface 34 also may be curved as described above in connection with FIGS. 4A and 4B. Displacement portion may be supported and positioned by spanning section 36, which is in turn supported by fixation portion 38. Spanning section 36 and displacement portion 32 may be configured and dimensioned to provide varying amounts of cantilever for the bearing surface 34. Such a cantilever can provide clearance for the fat pad and/or other critical tissues behind the implant. Fixation means 39 such as screw holes, spikes or bone ingrown facilitating elements may be included in fixation portion 38.

Figure 9D:
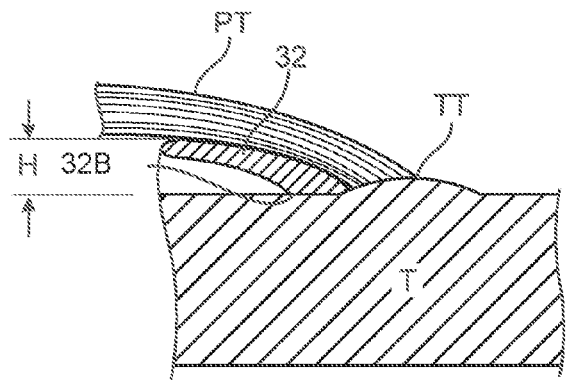
FIG. 9D is a cross-sectional view through section D-D of FIG. 9B.

Referring to FIGS. 9B and 9D, it can be seen that displacement portion 32 can be provided with a concavity on the bone-facing posterior side of displacement portion 32 that spaces the displacement portion away from the tibial, forming a space (S) therebetween with a height indicated by the double arrow. Space S preferably has a maximum height between an underside 32U of displacement portion 32 and the surface of the tibia in a range of about 5-25 mm, or more typically about 10-20 mm, in order to accommodate the fat pad and other tissues beneath the displacement portion 32. Displacement portion 32 has a supporting section 32B, as described above, that sits in engagement with the tibia in the space between the tibial tuberosity TT and the caudal edge of the fat pad, thereby supporting displacement portion 32. Height (H), the perpendicular distance between the bone engaging surface 326 of supporting section 32B and the apogee of bearing surface 34, as also described above, is shown in FIG. 9D.

To fit displacement portion 32 within the available space, with reference again to FIG. 9A, supporting section 32B preferably extends in the cranial-caudal direction a distance (SS) of no more than about 20 mm, usually being about 5-15 mm, more preferably about 8-12 mm. The cranial end 32C of displacement portion 32 preferably extends a distance (CE) of about 5-30 mm, typically about 10-25 mm, or more typically about 15-22 mm in the cranial direction from the upper (cranial) extent of supporting section 32B, which lies against the tibia approximately at dimension line (DL) in FIG. 9A The concave shape of the posterior side of displacement portion 32 causes its lateral margin 33 to extend around the lateral side of the tibia (if the fixation portion of the implant is mounted on the medial side). In some embodiments, for example as shown in FIG. 9B, lateral margin 33 may be configured to contact the tibia to provide additional support for the displacement portion and bearing surface in resisting forces applied by the patellar tendon, particularly at high flexion angles. An additional embodiment may have an additional fixation portion on the lateral end of the implant as shown in FIG. 9C, to provide additional support and stabilization for the implant.

Figure 10:
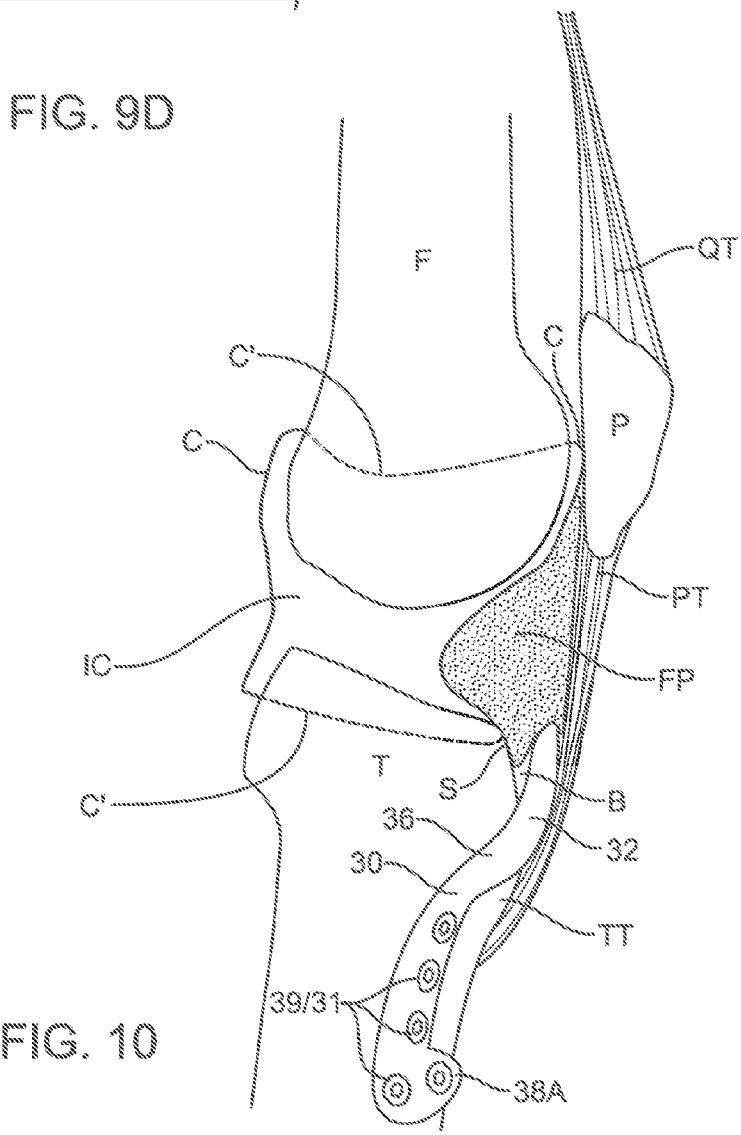
FIG. 10 is a schematic diagram of a human knee in side view illustrating positioning of an implant according to another disclosed embodiment.

FIG. 10 illustrates an embodiment of the present invention, such as implant 30 described above, after implantation on the tibia. In this embodiment, implant 30 also employs an extended fixation portion 38A for enhanced torque resistance as described in more detail below. Fixation portion 38A may have an extension portion that wraps around either the anterior or posterior side of the tibia, or both, to further stabilize the implant. Multiple screw holes 39 and bone screws 31 are used as dictated by patient anatomy and clinical factors such as condition of the bone.

Placement and fixation of an implant according to embodiments of the present invention can often be accomplished through a single surgical incision adjacent the patient's knee. The implant is then placed through the incision with the displacement portion inserted under the patellar tendon cranially with respect to its attachment point to the tibia at the tibial tuberosity. A therapeutic location that is a target area for placement of the displacement portion includes the caudal pocket below the infrapatellar fat pad containing the infrapatellar bursa (B). Reference letter (B) is provided in FIG. 10 to identify the target area, but the bursa itself is not shown because in some situations it may be necessary to remove part or all of the bursa to accommodate the implant. However, unlike the articular capsule or the infrapatellar fat pad, there are not significant potential negative indications associated with removal or dissection of the infrapatellar bursa.

Figure 1:
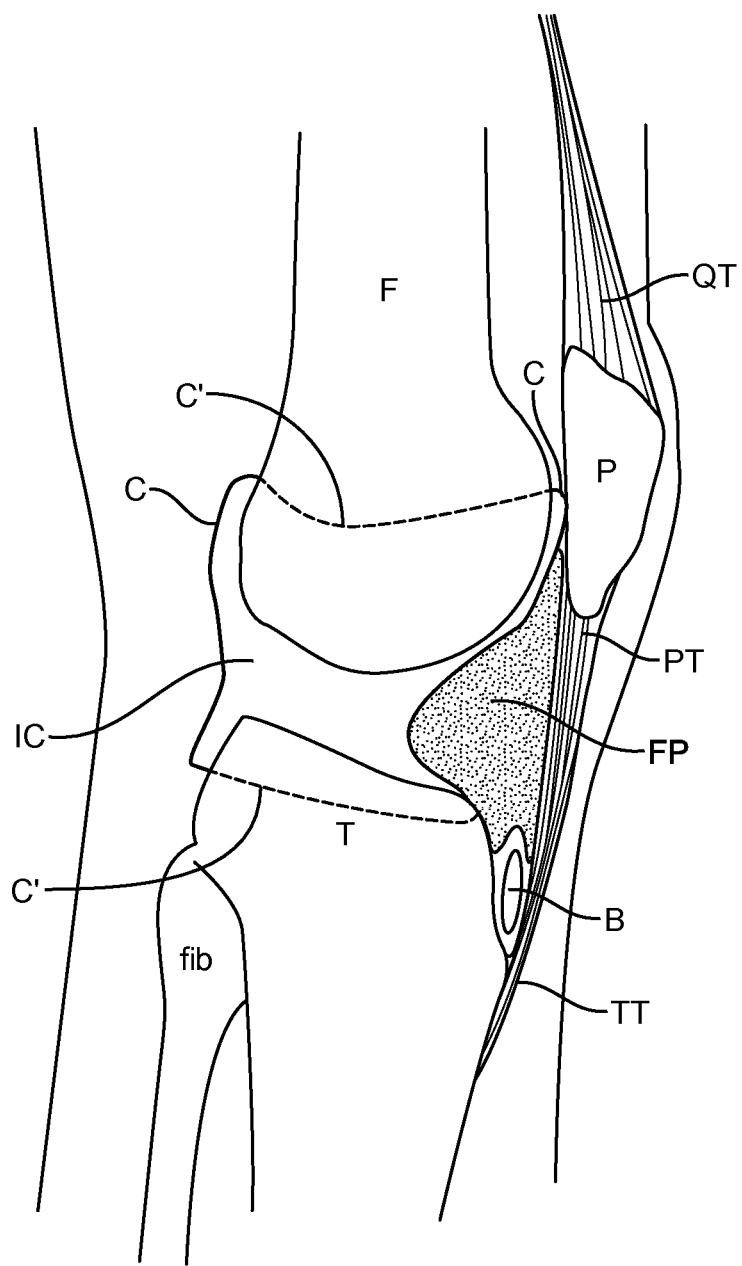
FIG. 1 is a schematic diagram illustrating anatomical features of a human knee joint in a side view.

Placement of the implant as shown for example in FIG. 10, allows the implant to be placed and fixed through a single incision without penetrating the capsule (C) or dissecting the infrapatellar fat pad (FP) or separating it from its attachment along the posterior of the patellar tendon (PT). Of course, depending on the shape and size of the implant as clinically determined by the surgeon, it may be necessary to push on and somewhat reposition the fat pad as indicated in FIG. 10 as compared to FIG. 1. Also, as previously described, the smooth, curved shape of the bearing surface 34 and displacement portion 32 moves the patella anteriorly and away from the femur while limiting the amount of movement caudally, thus reducing or avoiding a Baja effect. The shape of implant 30 also effectively avoids and preserves the natural attachment point of the patellar tendon (PT) to the tibia at the tibial tuberosity (TT).

FIG. 10 also further illustrates how the shape of the spanning section 36 and displacement portion 32 provides a cantilevered bearing surface 34 to define space (S) under the implant to accommodate the fat pad and its attachment to the side of the tibia. The cantilevered portion of the implant may be configured to deflect under high loading conditions to reduce strain on the tendon. Such deflection may be engineered into the implant by selection of shape, thickness and material so as to allow the implant to flex, or more active means such as springs or hydraulic cylinders may be used. In further alternatives, bearing surfaces of implants according to embodiments of the invention may include resilient elements such as fluid filled pillows and/or pressure control volumes utilizing check or relief valve systems.

Figure 11A:
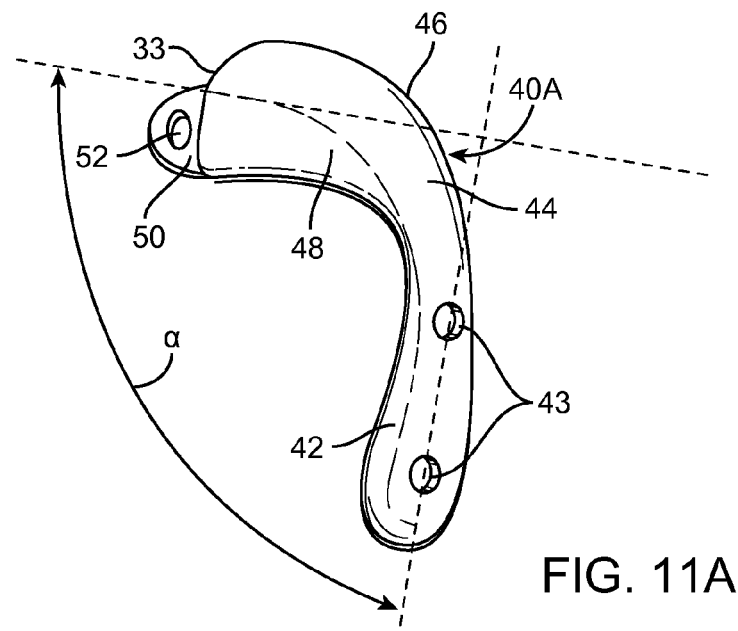
FIGS. 11A, 11B and 11C are perspective views of further alternative embodiments employing supplemental fixation/support means.
Figure 11B:
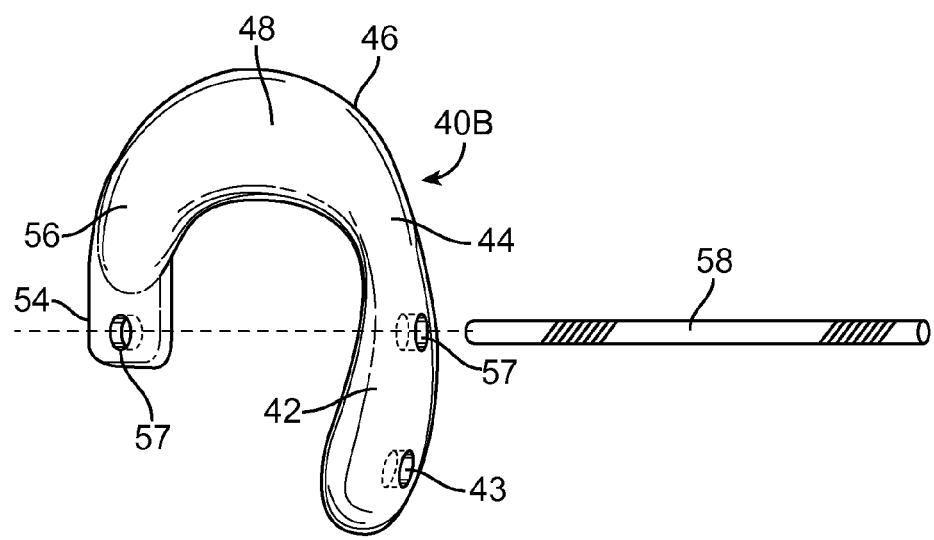
Figure 11C:
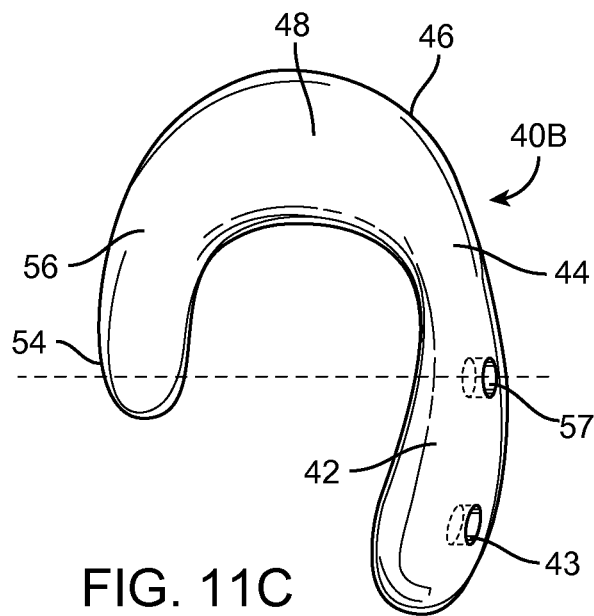
Figure 11D:
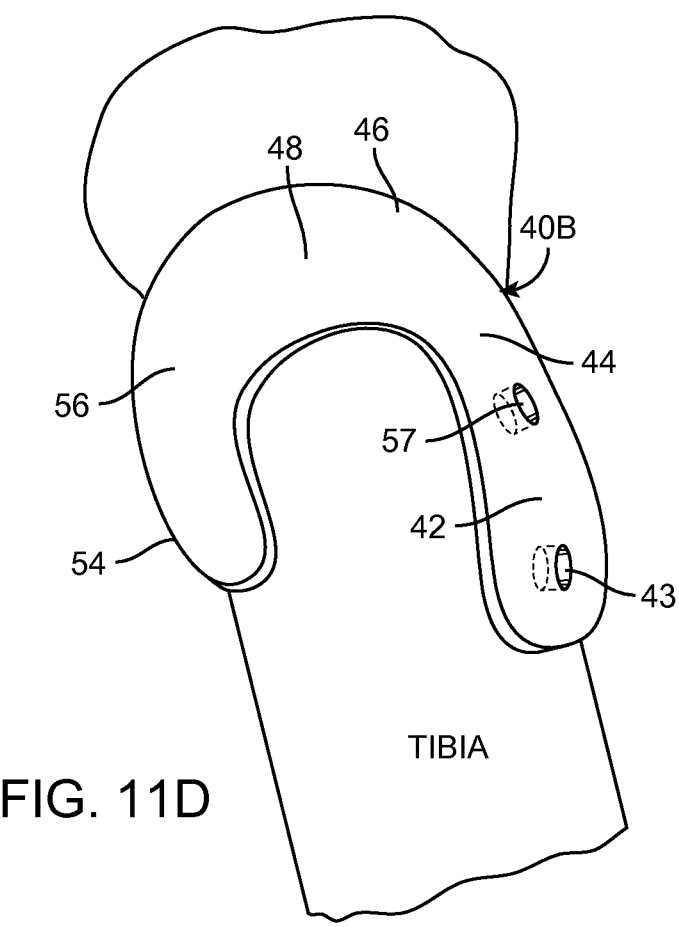
FIG. 11D is a schematic illustration of an embodiment such as shown in FIG. 11C in place on a portion of the tibia.

FIGS. 11A and 11B illustrate further alternative embodiments employing supplemental support and fixation elements 50 and 54. Implants 40A and 40B each include fixation portion 42 with fixation means such as bone screw holes 43, spanning section 44 and displacement portion 46 with bearing surface 48, all as previously described. Positioned at the end of displacement portion 46 on implant 40A is supplemental support and fixation tab member 50 with at least one bone screw hole 52. In some embodiments, implant 40A may be generally shaped in a manner similar to implant 30 of FIG. 9B, with tab member 50 disposed at the lateral margin 33 of the implant having a bone engaging surface in contact with the tibia. In other embodiments, the shape may be generally reversed such that tab member 50 would be disposed at a medial margin of the implant displacement portion. In a further embodiment shown in FIG. 11C, tab member 50 has no bone screw hole, but simply provides additional surface area resting against the tibial surface to stabilize the device and to more widely distribute the pressure of the device due to the force of the patellar tendon against the device.

The position of tab member 50 with respect to fixation portion 42 may necessitate a second surgical incision site when placing implant 40A. In order to provide supplemental fixation and support means without necessitating a second incision site, means such as shown in FIG. 11B for implant 40B may be alternatively employed. In this embodiment, displacement portion extension 56 extends the displacement portion in a caudal direction around the lateral side of the tibia (if the fixation portion 42 is mounted to the medial side of the tibia). Supplemental support and fixation tab 54 is disposed at the caudal and/or lateral margin of the extended displacement portion and provided with at least one fixation hole 57. To allow for placement and fixation from a single incision site, fixation hole 57 is configured to accommodate fixation rod 58 and is aligned with a corresponding fixation hole 57 in fixation portion 42. Fixation rod 58 may comprise a threaded rod or elongated bone screw, and fixation hole 57 may be threaded so as to receive the threaded tip of the fixation rod. In an alternative embodiment, fixation rod 58 may be threaded over its entire length with a pointed distal end and a bone screw head at the proximal end adapted to receive a torqueing tool such as a hex driver.

Placement of an embodiment such as implant 40B is achieved by positioning the fixation portion on one side of the tibial tuberosity with the extended displacement portion 56 extending around the attachment of the patellar tendon to the tibia and back down caudally on the opposite side of the tibial tuberosity. With fixation holes 57 thus aligned on opposite sides of the tibia, fixation rod 58 may be inserted through the same surgical incision and through a portion of the tibia to fix both holes 57 in a single operation. Additional fixation screws may be placed in other holes 43, again through the same surgical incision. A specialized drill guide might be employed to ensure accurate alignment while drilling the hole.

Figure 12A:
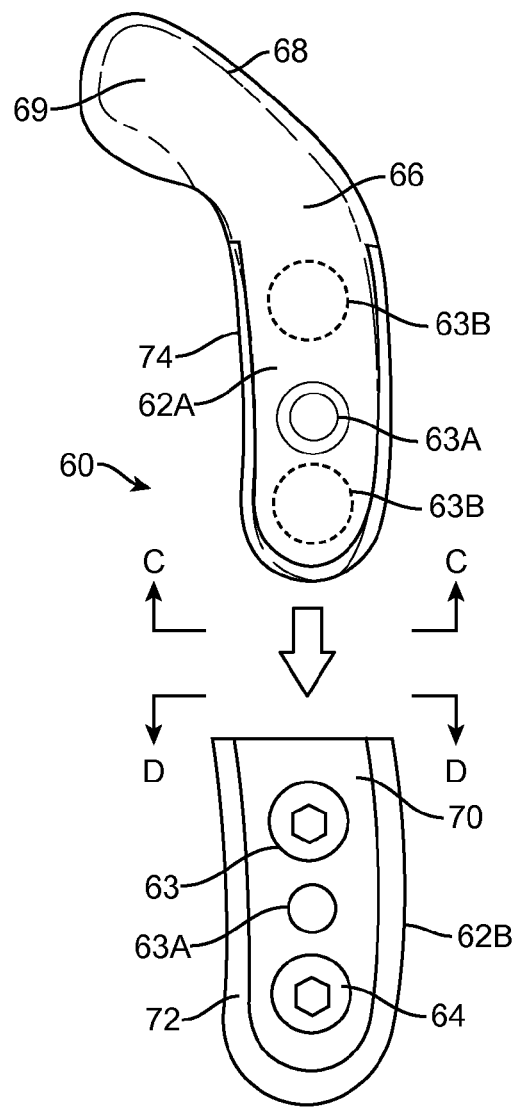
FIGS. 12A, 12B, 12C, 12D and 12E are various views of yet another alternative embodiment employing a separate fixation base member.

Depending on patient anatomy and other clinically determined parameters, placement of an implant according to embodiments of the present invention may present a challenge because of the torqueing forces exerted on the displacement portion after insertion under the patellar tendon, even before fixation means, such as bone screws, are secured. Such torqueing forces would tend to lift the fixation portion away from the bone surface to which it was to be affixed. In this situation, a separate fixation base may be employed as shown, for example, in FIGS. 12A-E. In this alternative embodiment, implant 60 has a fixation portion that comprises a body member fixation portion 62A and a base member fixation portion 62B. FIG. 12A shows the part unassembled before placement of the body member fixation portion 62A, and FIG. 12B shows the assembled parts as they may appear after placement.

Figure 12B:
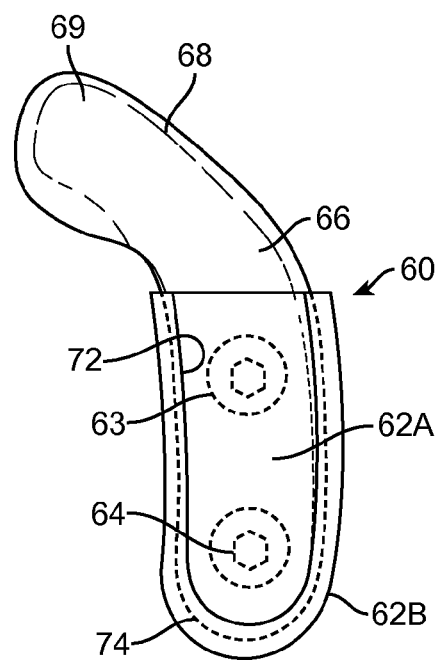

As shown in FIGS. 12A and 12B, implant 60 also includes spanning section 66 and displacement portion 68 with bearing surface 69 generally as previously described. In one embodiment, screw holes 63, configured to receive bone screws 64, are provided only in base member fixation portion 62B. In a further alternative embodiment, illustrated only in FIG. 12A, additional fixation screw holes 63A may be provided in both the base member and body member fixation portions and positioned so that the holes align when the body member is received in the base member. In another alternative embodiment, bone screw access holes 63B may be provided as discussed further below. Access holes 63B are shown in FIG. 12A in dashed lines as optional features.

Figure 12C:
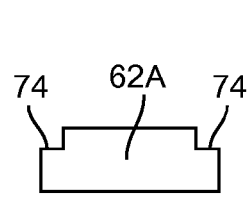
Figure 12D:
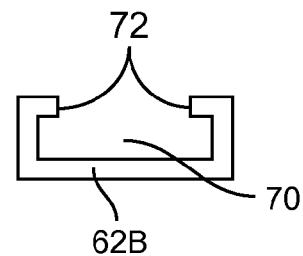

Body member fixation portion 62A and base member fixation portion 62B are provided with complementary, mating shapes to permit them to be securely fitted together. Persons of ordinary skill in the art may select from various complementary shapes, one example of which is shown in FIGS. 12C and 12D, which are end views at lines C-C and D-D, respectively, in FIG. 12A. In this exemplary embodiment, base member fixation portion 62B defines a channel 70 with retaining edge 72 that extends therearound. The complementary shape of body member fixation portion 62A is provided by guide channel 74, which in this exemplary embodiment extends around the caudal end and onto both sides of the body member fixation portion 62A. In other embodiments, separate mating features may be provided only on the sides, not extending around the caudal end of the implant.

The two-piece design of an embodiment such as implant 60 permits the base member fixation portion 62B to be first secured at a selected location without an eccentric or torqueing forces applied by the target tissue through the displacement portion 68. Fixation means such as holes 63 and bone screws 64 may be used to secure the base member fixation portion 62B. Once proper placement is confirmed, displacement portion 68 may be inserted under the target tissue, such as the patellar tendon, and then base member fixation portion 62A inserted into base member fixation portion 62B with a relatively straightforward sliding action as indicated by the arrow in FIG. 12A to provide a combined implant generally as shown in FIG. 12B. Screw holes 63 and screws 64 are shown in phantom lines in FIG. 12B because they are covered by body member fixation portion 62A. For this reason screws 64 preferably are low profile screws with flat heads to avoid interference with the body member when inserted into the base member. Channel 74 is also shown in phantom lines because it is received behind edge 72.

Figure 12E:
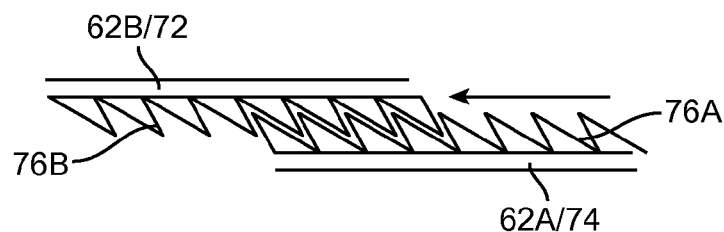

Various locking means for securing the body member to the base member are possible. One such locking means embodiment is schematically illustrated in FIG. 12E. In this illustrative embodiment, inter-engaging teeth 76A and 76B are provided on the facing surfaces, respectively, of the body member channel 74 and the base member retaining edge 72. When body member is inserted into the base member as indicated by the arrow in FIG. 12E, the inter-engaging teeth act in a ratchet-like manner, permitting insertion but preventing removal. In some embodiments, the teeth may themselves be formed with resiliency to permit insertion. In other embodiments, the teeth may be relatively short with less resiliency to permit insertion provided by elastic deformation of base member fixation portion 62B and retaining edge 72. For even greater fixation security, after the body member is fully received in the base member, additional bone screws may be inserted through optional, additional fixation screw holes 63A, which become aligned as described above.

It will also be appreciated by persons of skill in the art, that inter-engaging teeth or other ratchet-type locking means may be difficult to disengage if it becomes necessary to remove or reposition the base member during the initial implant procedure or a later intervention. Disengagement may be achieved, for example, by deformation of base member fixation portion 62B and retaining edge 72. In one alternative, bone screw access holes 63B may be provided in body member fixation portion 62A as shown in FIG. 12A. Access holes 63B are positioned to align with bone screw holes 63 in base member fixation portion 62B when the body member is received in the base member after implantation. Using access holes 63B, bone screws 64 may be removed without separating the body member from the base member.

In another alternative embodiment, inter-engaging or ratchet-type locking means is not provided. Instead, locking means may be provided by one or more additional fixation screw holes 63A. In such an embodiment, body member fixation portion 62A may be freely inserted and removed from base member fixation portion 62B once the base member is installed. The complementary shape of the mating parts as described initially carries the torqueing force of the target tissue acting on displacement portion 68 and then the two members are locked together using bone screws through one or more additional fixation screw holes 63A. Bone screw access holes 63B also may be included as desired to provide further removal options.

Figure 12F:
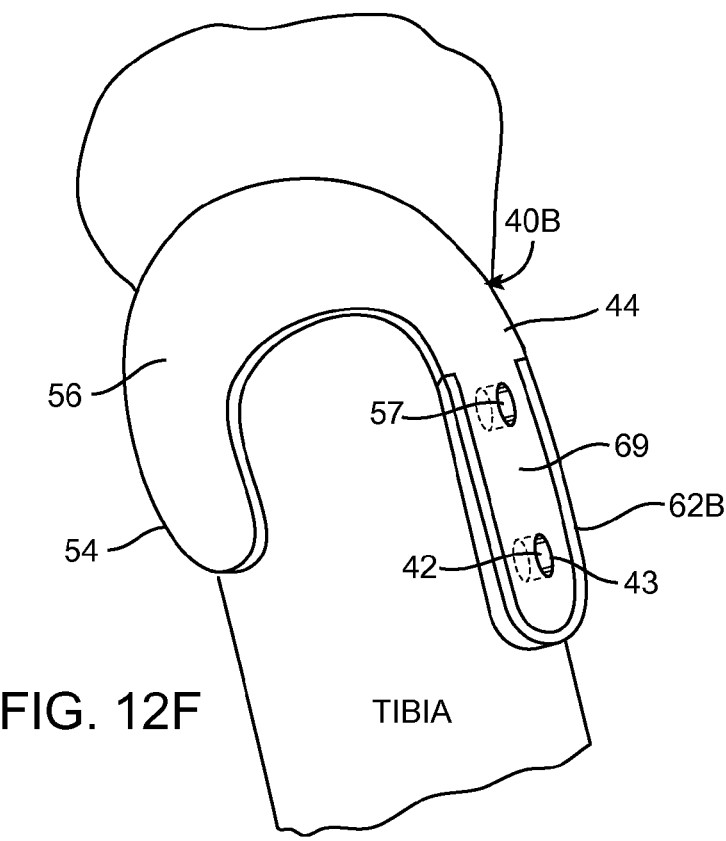
FIG. 12F is a schematic illustration of a further alternative embodiment, also employing a separate fixation base in place on a portion of the tibia.

FIG. 12F shows an additional alternative body member-base member geometry, with a curved interface between the parts which allows adjustment for any variation in the angle of the tibial surface against the fixation portion. This allows the body member 69 to be positioned so that the posterior edge of the displacement section rests firmly against the tibia as the fixation screws are tightened.

Figure 13A:
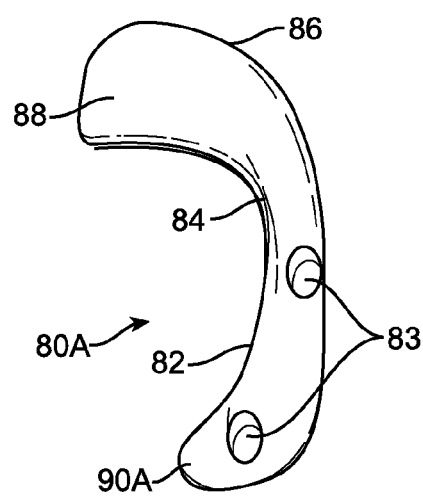
FIGS. 13A, 13B, 13C, 13D and 13E are views of other alternative embodiments having differently shaped fixation portions.
Figure 13B:
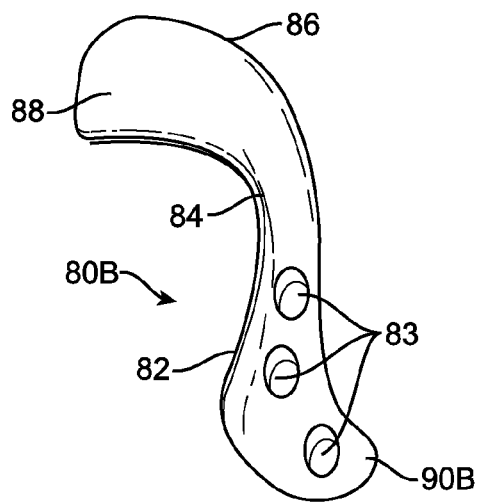

As mentioned above, torqueing and other complex forces applied to the fixation portion through the target tissue acting on the displacement portion may be significant. In order to better resist such forces various supplemental fixation and support embodiments may be provided. Two such exemplary embodiments have been described above in connection with FIGS. 11A and 11B. Additional exemplary embodiments are shown in FIGS. 13A-E. Implants 80A-E of FIGS. 13A-E each include fixation portion 82 with screw holes 83, spanning section 84 and displacement portion 86 with bearing surface 88 generally as previously described. In addition to these basic structures, implant 80A may include extension portions extending from fixation portion 82 in a direction generally transverse to that of fixation portion 82. For example, as shown in FIG. 13A, an extension portion 90A may be configured to extend generally in the same direction as the displacement portion, e.g., if the fixation portion 82 is mounted on the lateral side of the tibia, in a medial direction (or angled medially and caudally), across the anterior surface of the tibia transverse to the longitudinal axis of fixation portion 82, but caudally of the tibial tuberosity. In another alternative, as shown in FIG. 13B, implant 80B includes extended fixation portion 90B, which extends in a direction opposite from the displacement portion 86, e.g. laterally, or laterally and caudally, relative to fixation portion 82 so as to extend around the lateral side of the tibia. In another example, if the fixation portion 82 is mounted to the medial side, extended fixation portion 90B may be configured to extend posteriorly further around the medial and/or posterior side of the tibia (if the fixation portion 82 is mounted to the medial side). Extended fixation portions 90A and 90B create a wider base for fixation portion 82 and thus provide greater resistance to torqueing forces as described. Extended fixation portions 90A and 90B generally will be configured and dimensioned to match the shape of the tibia in the area of contact.

Figure 13C:
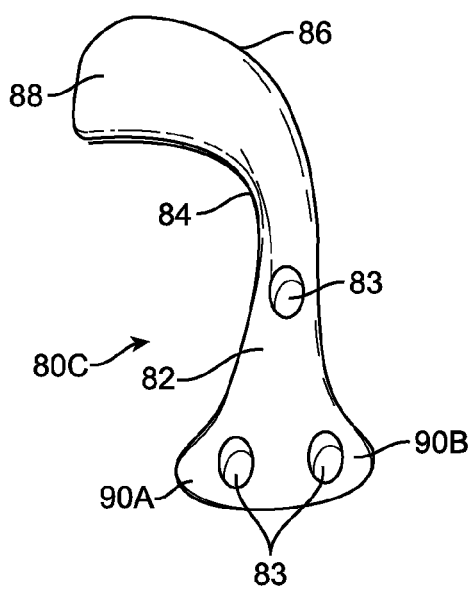
Figure 13D:
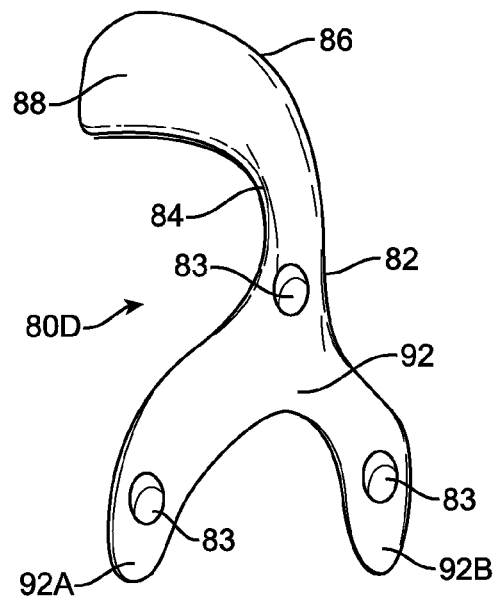

An extended fixation portion configured and positioned as extended fixation portion 90A will help to resist torqueing applied to the displacement portion 86 by creating a greater surface bearing against the bone at a greater distance from the center of rotation of the torqueing force, which will lie approximately along a centerline of fixation portion 82. An extended fixation portion configured and positioned as extended fixation portion 90B will help to resist torqueing force applied to the displacement portion 86 by creating a greater lever arm through which a bone screw in fixation holes 83 may act to resist the torqueing force. In some situations it may be desirable to utilize both extended fixation portions 90A and 90B to achieve the benefits of both approaches. FIG. 13C shows exemplary implant 80C employing both laterally- and medially-extended fixation portions 90A, 90B on one device.

Depending on patient anatomy, it may be desirable to provide a fixation portion that wraps farther around the tibia. In such situations, a split or bifurcated fixation portion 92 may be employed such as shown with implant 80D in the exemplary embodiment of FIG. 13D. In this embodiment, split fixation portion 92 forms two fixation arms 92A and 92B at its caudal end, one extending laterally and posteriorly, and a second extending medially and anteriorly, that can be configured to wrap around the tibia in opposing directions to the extent appropriate for the patient anatomy and clinical situation presented. These fixation arms 92A, 92B can be oriented transverse to longitudinal axis of fixation portion 92 to extend primarily in the medial-lateral direction, or angled caudally as wells as medially or laterally. Alternatively, a single arm 92A or 92B may be employed in a manner similar to the exemplary embodiments of FIGS. 13A and 13B employing single extended fixation portions 90A or 90B. In addition, the caudal ends of fixation arms 92A, 92B may have holes configured to receive a rod or screw extending through one fixation arm 92A and through the tibia to the other fixation arm 92B.

Figure 13E:
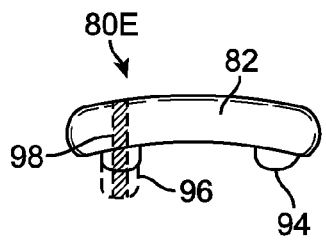

Again, depending on patient anatomy, it also may be desirable to provide differently shaped bone facing fixation surfaces for fixation portion 82. Alternatives include fixed protrusions 94 and adjustable protrusions 96 as illustrated in FIG. 13E. Such protrusions allow the fixation portion 82 to contact the bone at discreet locations to accommodate variability in the contour of the bone surface. Fixed protrusions may be ground to a desired height and shape according to the anatomy of each patient to provide further patient specific adaptability. Adjustable protrusions may be provided with an adjustment mechanism 98, such as a threaded member accessible at the outer surface of fixation portion 82 and rotatable to move adjustable protrusions 96 between an inner position and an outer position (shown in dashed lines in FIG. 13E) to adjust the distance the protrusion extends from the fixation portion 32. Alternatively or additionally, fixed or adjustable protrusions may be provided on the bone-facing side of the displacement portion such that it contacts the bone at discrete locations, accommodating variations in shape of the bone surface on the cranial side of the tibial tuberosity where the displacement portion extends under the patellar tendon.

The present disclosure contains multiple alternative embodiments and multiple alternative features within each disclosed embodiments. As will be apparent to persons of ordinary skill in the art based on the teachings herein contained, different features may be employed with embodiments other than those on which they are shown in the drawings for purposes of illustration. Given the number of possible combinations, it is not possible within a concise disclosure to separately illustrate each combination of features as would be understood by those skilled in the art. As non-limiting examples, each of the different supplemental fixation or support means shown in FIG. 11A or 11B, the fixation base member shown in FIGS. 12A-E, and/or the different fixation portion shapes shown in FIGS. 13A-13E may be used together in different combinations or individually with each different implant herein.

Figure 14A:
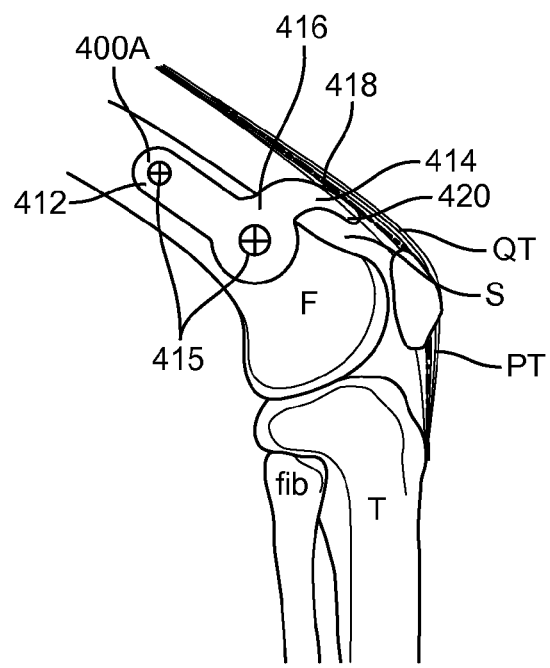
FIGS. 14A and 14B are schematic illustrations of further alternative embodiments adapted for femoral fixation.
Figure 14B:
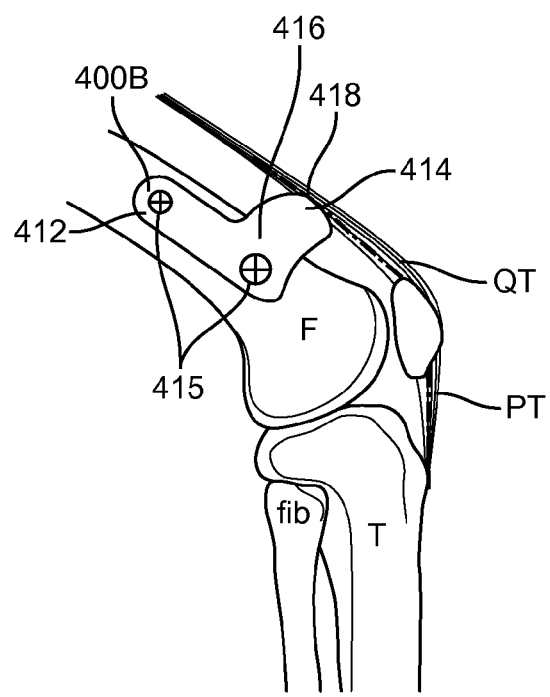

FIGS. 14A and 14B depict further exemplary embodiments of implants 400A and 400B, respectively, also for treating patellofemoral osteoarthritis and/or patellar maltracking, but with femorally mounted implants as shown. As with other embodiments disclosed herein, implants 400A and 400B each have a fixation portion 412 including one or more holes 415 for receiving screws, or other fixation means for anchoring the implant to bone. Fixation portion 412 is generally straight and elongated, being configured for positioning in general alignment with the femoral shaft on the lateral, medial or anterior-medial/lateral side of the femur, cranially with respect to the patella. Holes 415 may be positioned in approximate alignment with a longitudinal centerline of fixation portion 412 as shown, however additional holes may be included for added fixation security, similar to embodiments shown, inter alia, FIG. 10 or 13A-D. Preferably fixation portion 412 is configured to be mounted to the femur outside the joint capsule, cranially with respect to the tendons, ligaments and other tissues that form the capsule.

Displacement portion 414, is configured and dimensioned to be positioned under the quadriceps tendon caudally separated from the insertion point of the tendon in the quadriceps muscle and cranially with respect to its attachment point to the patella, with the entire displacement portion 414 preferably being disposed entirely outside the joint capsule. Thus, for a medially placed implant displacement portion will also extend laterally across an anterior portion of the femur. Likewise, a laterally placed device will have a displacement portion 414 that also extends medially across an anterior portion of the femur. The displacement portion 414 is configured to atraumatically engage the quadriceps tendon and displace it anteriorly relative to the femur, thus increasing space in the patellofemoral area. The displacement portion 414 has a width in the lateral-medial direction selected to accommodate the full width of the quadriceps tendon so that the tendon remains engaged along its entire width as it slides on the displacement portion. Displacement portion 414 has a length in the caudal-cranial direction selected so that it does not interfere with the patella. Displacement portion 414 preferably has a convex curvature on bearing surface 418, which engages the tendon. In general, the displacement portion and, in particular the bearing surface of the displacement portion, will be free of holes or other fixation means, with configuration similar to the bearing surfaces in other described embodiments.

As with tibial mounted embodiments, the displacement portion 414 and/or bearing surface may have a curvature which provides a constant displacement of the tissue throughout the range of motion of the joint, or configured to vary the displacement at different points throughout the range of motion. The curvature may be entirely or partially spherical, elliptical, parabolic, logarithmic spiral, or other curvature or combination thereof. In preferred embodiments the displacement portion 414 is configured such that a cranial aspect of bearing surface 418 slopes or curves gradually away from the femur as it extends in the caudal direction to provide gradually increasing displacement of the tendon.

A spanning section 416 interconnects fixation portion 412 and displacement portion 414. Spanning section 416, is previously described to appropriately position the displacement portion with respect to the fixation portion and soft and bony tissues in the area of treatment. As with other embodiments, displacement of the target tissue can be altered by changing the length, curvature and angle of the spanning section among other features. Implant 400A (FIG. 14A) may also include a cantilevered portion 420 of displacement portion 414 which has an undercut surface that is spaced apart from the underlying femoral surface. As with other described embodiments, cantilevered portion 420 creates a space (S) between the implant and the bone to accommodate soft tissue structures as needed. Cantilevered portion 420 also extends the displacement portion 414 in the caudal direction toward the patella to optimize displacement while minimizing interference with the joint capsule and other soft tissues. Alternatively, implant 400B, shown in FIG. 14B, may be configured without a cantilevered portion such that substantially all of the bearing surface 418 overlies and is supported by portions of the displacement portion 414 that engage the femur.

Implants 400A, 400B may optionally include various other features described above in connection with tibial-mounted embodiments. For example, implants 400A and 400B may include a supporting section extending from a cranial part of the underside of the displacement portion into and merging with the fixation portion as described above in connection with tibially mounted embodiments. The configuration of a supporting section in these embodiments will, however, be generally inverted to accommodate fixation on the femur cranially with respect to the patella, as opposed to, on the tibia, caudally with respect to the patella. Implants 400A, 400B may alternatively have a tab or extension portion extending cranially, medially, and/or posteriorly from the displacement portion 414 on the opposite side from the fixation portion 412 which can engage the femur to provide additional support for the displacement portion 414. As with the embodiments shown in FIGS. 11A and 11C, such tab or extension may include a hole through which a bone screw may be inserted into the bone, or a hole for receiving a rod or screw extending from fixation portion 412 through the femur.

Figure 15A:
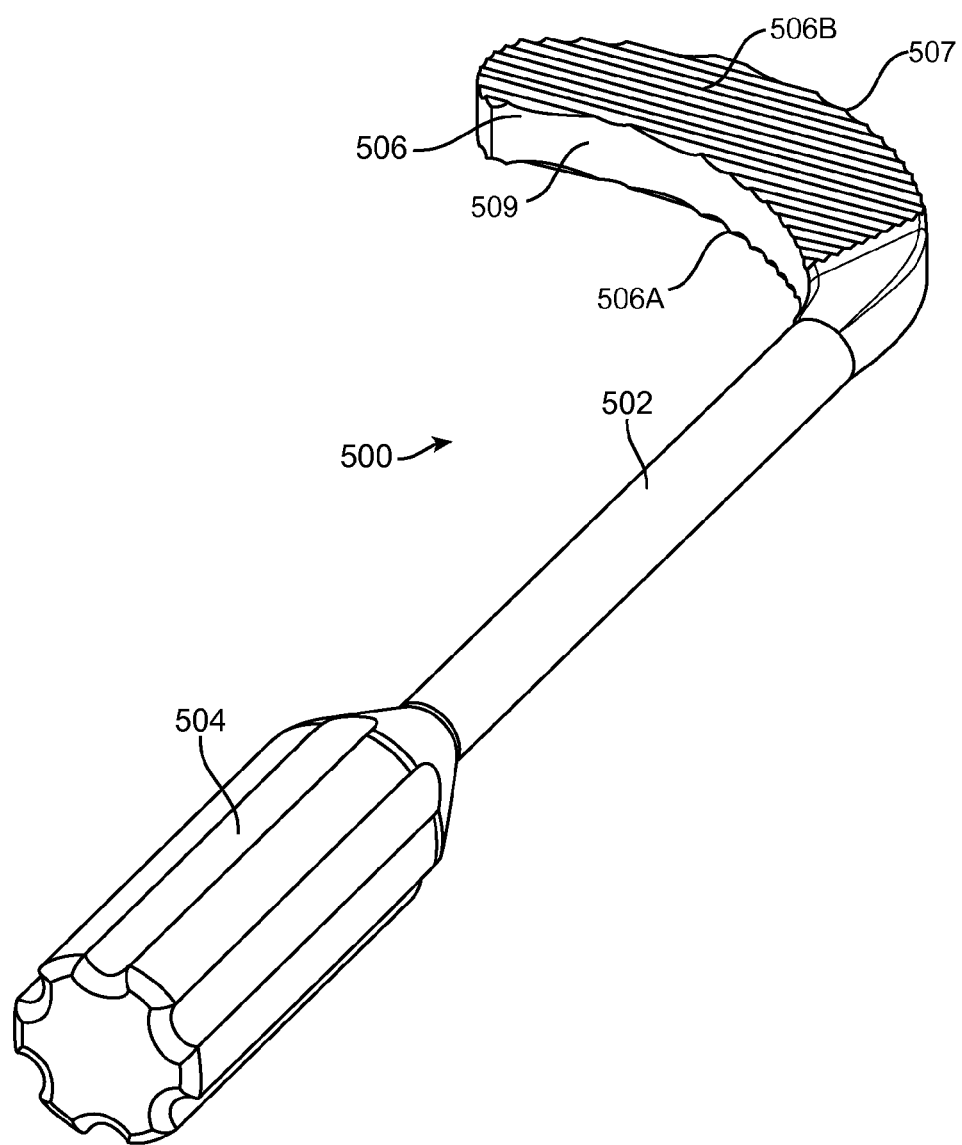
FIGS. 15A and 15B are views of an embodiment of disclosed instrumentation useful in procedures for placement of implants disclosed herein.
Figure 15B:
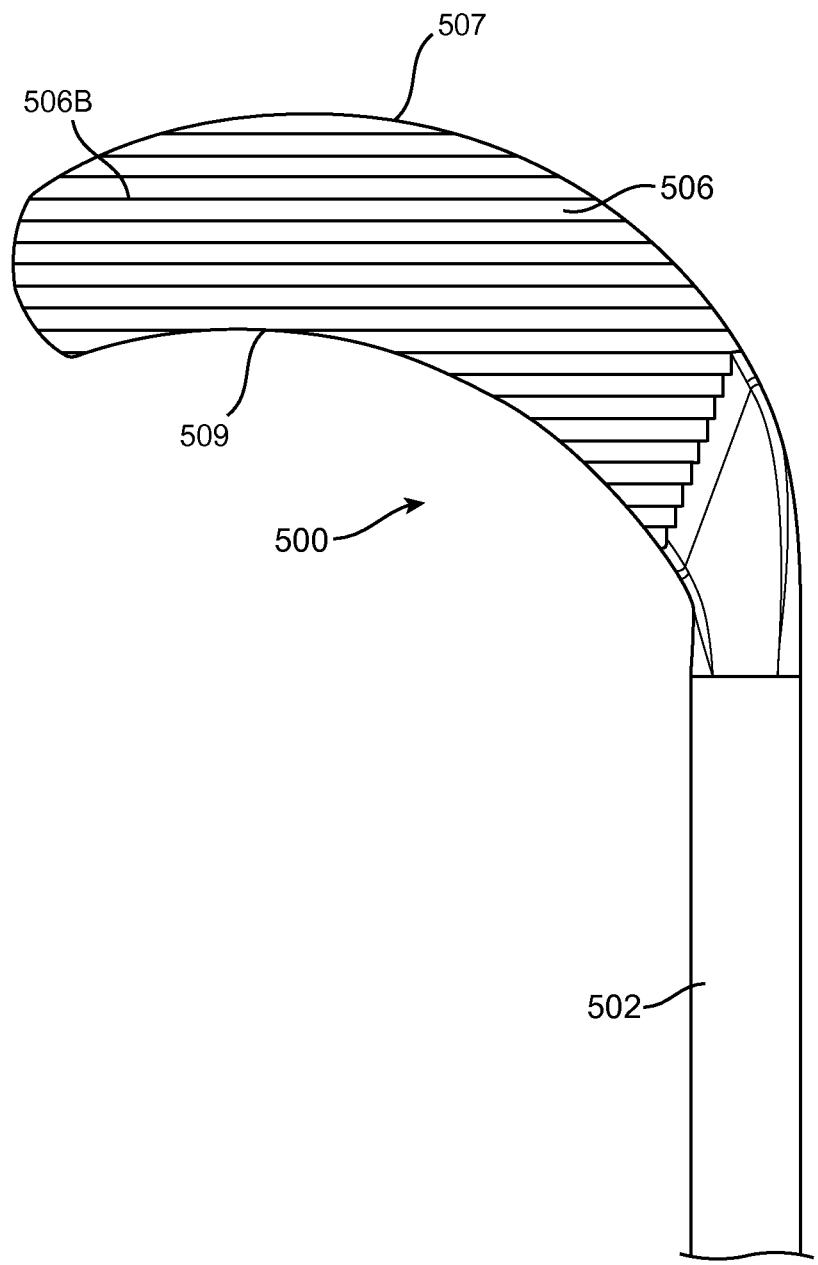

In general, implants according to embodiments of the present invention may be positioned and fixed using well-known instrumentation that is used for other orthopedic implant procedures. However, because of the unique position and seating of embodiments of the present invention, a specially shaped curved file as shown in FIGS. 15A and 15B may be useful for preparing the bone surface at the implant location, particularly for tibially mounted implants. Curved file 500 comprises a shaft 502 with a handle 504 at a proximal end and a curved file element 506 at the opposite, distal end. File element 506, preferably made of a metal suitable for filing bone, extends in a transverse direction from shaft 502 and has a lower surface 506A and an upper surface 506B, one or both of which have grooves, knurling, points, bumps, or other features configured to file the bone surface to give it a suitable shape for receiving the implants of the invention. File element 506 is preferably curved about a second axis extending in a direction transverse to shaft 502 longitudinal axis in an anterior-posterior direction, giving file element 506 a convex cranial side 507 and a concave caudal side 509. Upper and lower surfaces 506A, 506B are disposed at least partially in respective planes which are intersected by the second axis. In addition, lower and/or upper surfaces 506A, 506B may have a curvature about a third axis parallel to the longitudinal axis of shaft 502. This latter curvature may have various shapes, e.g. generally matching the curvature of the anterior surface of the tibia in the region just cranial to the tuberosity where the implant will be fixed, or a different curvature as is suitable to provide a stable base for the implant. Further, either or both the convex cranial side 507 or concave caudal side 509 may have grooves or other features to facilitate filing the bone with these surfaces. Moreover, the lower and/or upper surfaces 506A, 506B may have either a convex or concave curvature about an axis transverse to shaft 502 as may be suitable to create the particular shape desired for the bone surface. The file element 506 may be inserted through an incision on the lateral or medial side of the tibia just cranial to the tibial tuberosity such that the file element extends across the anterior tibial surface. File 500 may be drawn back and forth in a cranial-caudal direction (parallel to the tibial shaft), or in a medial-lateral direction, to file down the tibial surface cranially of the tuberosity to the desired shape. It should be noted that in addition to their use in implanting the implants of the invention, the files disclosed herein may be used for other treatments, including bone re-shaping for the treatment of Osgood-Schlatter disease or other diseases.

Figure 16:
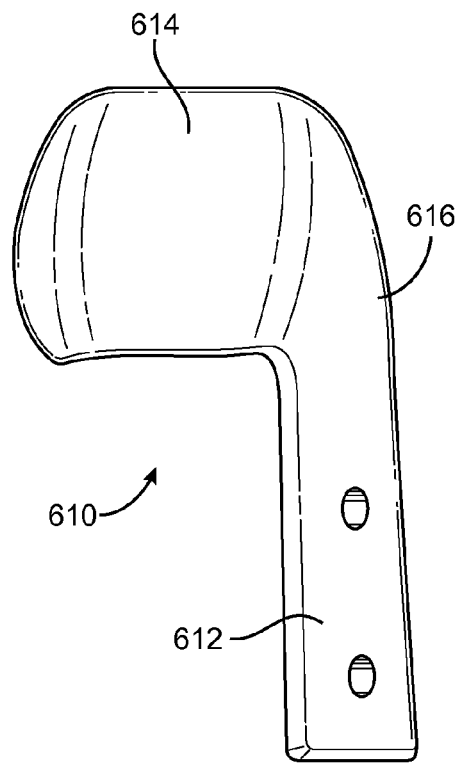
FIG. 16 is a drawing of another alternative embodiment viewed from the anterior aspect of an implant with a configuration generally as described herein.
Figure 17:
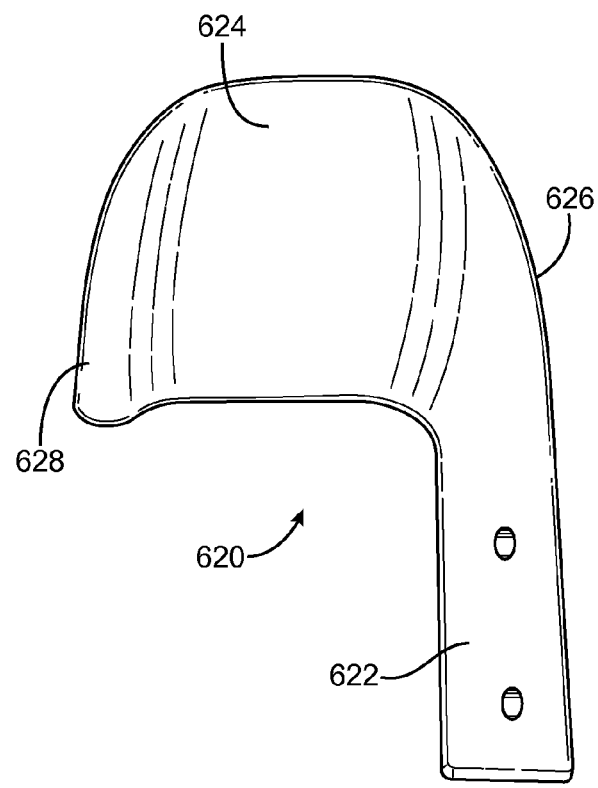
FIG. 17 is a drawing of another alternative embodiment viewed from the anterior aspect of an alternative implant including features similar to the embodiment shown in FIGS. 9A and 9B.
Figure 18:
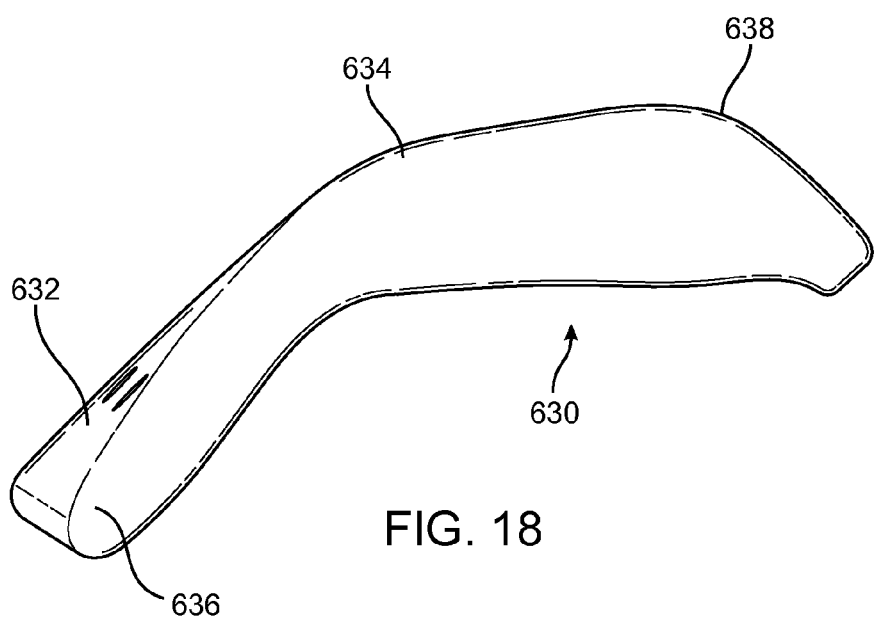
FIG. 18 is a drawing of another alternative embodiment viewed from a cranial aspect of another alternative implant with a displacement portion having an increasing thickness.
Figure 19:
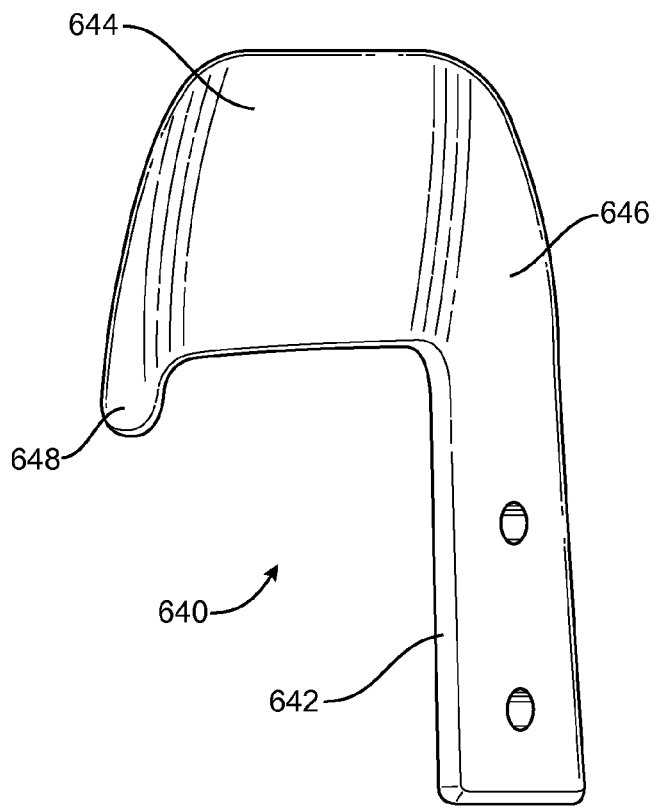
FIG. 19 is a drawing of another alternative embodiment viewed from an anterior aspect of a further alternative implant including features similar to the embodiments shown in FIGS. 11B and 11C.
Figure 20:
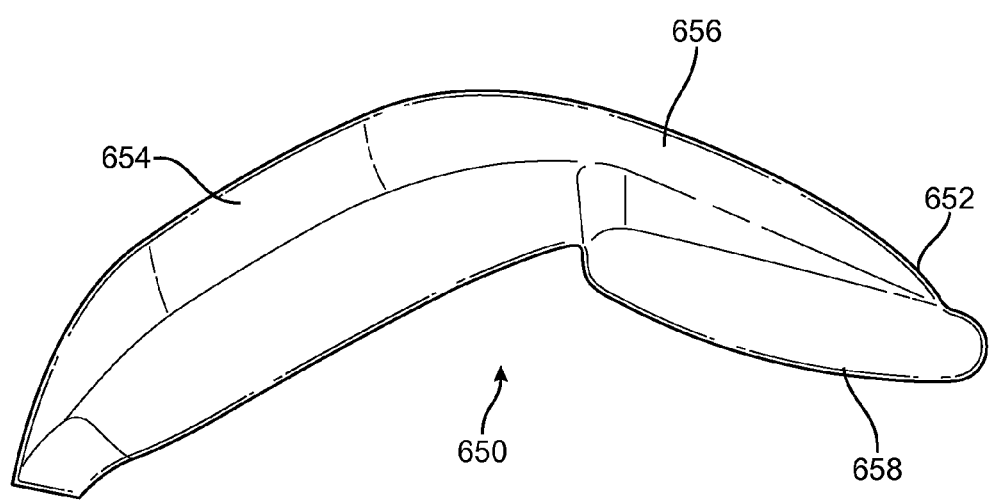
FIG. 20 is a drawing of another alternative embodiment viewed from a caudal aspect of yet another alternative implant with features to facilitate positioning prior to fixation.

FIGS. 16-20 illustrate further exemplary implants made according to the teachings of the present disclosure. For example, implant 610 in FIG. 16 is made according to the general teachings of the disclosure and includes, inter alia, fixation portion 612, displacement portion 614 and spanning section 616, as well as other features described herein for the various embodiments. Implant 620, shown in FIG. 17, includes a fixation portion 622, displacement portion 624 and spanning section 626, wherein displacement portion 624 is extended laterally as compared to implant 610 so that the lateral edge 628 of displacement portion 624 may be supported on the tibia, for example on Gerdy's tubercle or adjacent thereto, to provide a supplemental support element. In this regard, implant 620 includes features similar to embodiments shown in FIGS. 9A-D. Implant 630, shown in FIG. 18, also includes a fixation portion 632, displacement portion 634 and spanning section 636. Displacement portion 634 has a gradually increased thickness area 638 towards the lateral end in order to increase the tendon displacement at the lateral side. Implant 640, shown in FIG. 19, includes fixation portion 642, displacement portion 644 and spanning section 646. In this embodiment, displacement portion 644 includes lateral pad 648 at an outer end to provide supplemental support and fixation adjacent the tibial tubercle. In this regard, implant 640 may include features similar to embodiments shown in FIGS. 11B and 11C. Additionally, lateral pad 648 may be designed to hook the tibial tubercle. Implant 650, shown in FIG. 20, includes fixation portion 652, displacement portion 654 and spanning section 656. Fixation portion 652 has a bone engaging surface 658 formed with a convex profile to facilitate positioning along the tibial tuberosity prior to fixation. The convex profile may be in the range of about 10 degrees of convexity.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:
1. A prosthesis for treating disorders of the knee in the patellofemoral compartment of the knee, the prosthesis comprising:
 a fixation portion configured to be mounted to the tibia at a fixation site proximate the upper tibial extremity and medially or laterally of the tibial tuberosity;

a spanning section configured and dimensioned to extend cranially and laterally or medially from the fixation portion in a direction towards the tibial mid-line; and a displacement portion having an overall curvature around an axis generally parallel to the tibial shaft when the fixation portion is mounted at the fixation site and configured and dimensioned to (i) extend from the spanning section further laterally or medially under patellar tendon and in engagement therewith, and (ii) displace the patellar tendon anteriorly sufficiently to alter the location, angle or magnitude of forces exerted thereby on the patella so as to achieve a therapeutic effect in patellofemoral compartment of the knee.

2. The prosthesis of claim 1, wherein the therapeutic effect comprises a reduction of loading on an articular surface in the patellofemoral compartment of the knee.

3. The prosthesis of claim 1, wherein:
the displacement portion has a base portion configured to engage at least in part an anterior surface of the tibia and a cantilevered portion extending from the base portion to a free end, the cantilevered portion being configured to be spaced apart from the tibia when the base portion is engaging the tibia;
the displacement portion includes a bearing surface configured to atraumatically engage the patellar tendon, the bearing surface being free of holes or other fixation means; and
said base portion and said cantilevered portion e formed with said curvature around a common axis generally parallel to the tibial shaft.

4. The prosthesis of claim 1, wherein said displacement portion and spanning section are configured and dimensioned in combination to displace the patellar tendon from a pre-treatment anatomical path by displacement distance of more than about 5 mm and less than about 30 mm when the fixation portion is mounted to the tibia.

5. The prosthesis of claim 4, wherein said displacement portion and spanning section are further configured to position the displacement portion to define a space between at least a part of the displacement portion and the tibial surface.

6. The prosthesis of claim 5, wherein said displacement portion is configured and dimensioned to form a cantilevered structure with respect to the tibial surface with said space positioned under at least a portion of the cantilevered structure of the displacement portion when the fixation portion is mounted to the tibia.

7. The prosthesis of claim 6, wherein said space is further defined by a cranially-facing undercut in the displacement portion.

8. The prosthesis of claim 5, wherein:
the displacement portion has an outer end opposite the spanning section with said outer end including a supplemental support element having a bone engaging surface configured and dimensioned to rest against the tibia to support said displacement portion.

9. The prosthesis of claim 8, wherein said space is defined in an area between the spanning section and bone engaging surface of the displacement portion outer end.

10. The prosthesis of claim 8, further comprising a bone fixation element cooperating with said supplemental support element.

11. The prosthesis of claim 10, wherein said bone fixation element comprises at least one bone screw hole in said supplemental support element.

12. The prosthesis of claim 8, wherein said displacement portion and supplemental support element lie along a displacement portion axis at an angle of about 80-135 degrees with respect to a fixation portion axis.

13. The prosthesis of claim 8, wherein the displacement portion outer end extends in a caudal direction, with the displacement portion configured to extend around the tibia to an opposite side of the tibia from the fixation portion.

14. The prosthesis of claim 13, wherein the supplemental support element includes at least one fixation hole aligned with at least one bone screw hole in the fixation portion, said fixation hole and said bone screw hole configured to receive a single fixation rod extending therethrough.

15. The prosthesis of claim 8, wherein:
the fixation portion comprises a body member and a separate base member to which the body member may be coupled, said body and base members having complementary, mating shapes to provide a secure coupling of the body member to the base member; and
the separate base member includes plural bone screw holes for fixation to the tibia.

16. The prosthesis of claim 15, further comprising locking means for securing the fixation portion body member to the fixation portion base member.

17. The prosthesis of claim 1, wherein:
the fixation portion is disposed at an angle with the spanning section such that with the prosthesis implanted and the displacement portion engaging the patellar tendon, the fixation portion is substantially aligned with the tibial shaft;
the spanning section is configured and dimensioned to avoid contact with the medial edge of the patellar tendon; and
the displacement portion is further configured and dimensioned to lie substantially parallel to the axis of the tibial plateau when the fixation portion is secured medially of the tibial tuberosity with the fixation portion substantially aligned with the tibial shaft.

18. The prosthesis of claim 1, wherein:
the fixation portion comprises a body member and a separate base member to which the body member may be coupled, said body and base members having complementary, mating shapes to provide a secure coupling of the body member to the base member; and
the separate base member includes plural bone screw holes for fixation to the tibia.

19. The prosthesis of claim 18, wherein the fixation portion body member includes at least one bone screw access hole positioned to align with a bone screw hole in the fixation portion base member when said body member is fit with the base member.

20. The prosthesis of claim 18, further comprising locking means for securing the fixation portion body member to the fixation portion base member.

21. The prosthesis of claim 20, wherein said locking means comprise inter-engaging surfaces on said base and body members.

22. The prosthesis of claim 20, wherein said locking means comprises at least one bone screw hole extending through both said base and body members.

23. The apparatus of claim 1, wherein the fixation portion includes alterable protrusions on a bone facing surface, said protrusions being alterable to match bone surface contour at a fixation site.

24. A prosthesis for repositioning a target tissue, the target tissue comprising a connective tissue or muscle relative to a bone on which said target tissue acts, and the prosthesis comprising:

a fixation portion having one or more fixation features configured to receive fixation elements for securing the implant to the bone; and a displacement portion having a first end connected to the fixation portion and a free end opposite the first end, the displacement portion having a bearing surface configured to atraumatically engage and reposition the target tissue relative to the bone;

wherein the displacement portion has a base portion configured to engage the bone and a cantilevered portion extending from the base portion to the free end, the cantilevered portion being configured to be spaced apart from bone when the base portion is engaging the bone, the base portion and the cantilevered portion each having a curvature formed around a common axis parallel to a longitudinal axis of the bone when the fixation portion is secured thereto.

25. The implant of claim 24, wherein the displacement portion is at least partially ramp-shaped such that, when implanted, a lower part of the displacement portion has a first height relative to the bone surface and an upper part of the displacement portion has a second greater height relative to the bone surface, the ramp-shaped portion facing in a direction generally away from the free end.

26. The implant of claim 24, wherein the displacement portion is connected to the fixation portion at an end opposite the free end by a spanning section.

* * * * *